US005840744A

United States Patent [19]
Borgman

[11] Patent Number: 5,840,744
[45] Date of Patent: *Nov. 24, 1998

[54] INTRAVAGINAL TREATMENT OF VAGINAL INFECTIONS WITH BUFFERED METRONIDAZOLE COMPOSITIONS

[75] Inventor: Robert J. Borgman, Mundelein, Ill.

[73] Assignee: Minnesota Mining and Manufacturing Co., St. Paul, Minn.

[ * ] Notice: The term of this patent shall not extend beyond the expiration date of Pat. No. 5,536,743.

[21] Appl. No.: 680,750

[22] Filed: Jul. 15, 1996

Related U.S. Application Data

[63] Continuation of Ser. No. 295,242, Aug. 24, 1994, Pat. No. 5,536,743, which is a continuation-in-part of Ser. No. 950,827, Sep. 24, 1992, abandoned, which is a continuation-in-part of Ser. No. 362,273, Jun. 6, 1989, abandoned, which is a continuation-in-part of Ser. No. 144,252, Jan. 15, 1988, Pat. No. 1,837,378.

[51] Int. Cl.$^6$ .................................................. A61K 31/415
[52] U.S. Cl. .......................... 514/398; 514/944; 514/967
[58] Field of Search ..................................... 514/398, 944, 514/967

[56] References Cited

U.S. PATENT DOCUMENTS

| 4,472,376 | 9/1984 | Kamashita | 424/81 |
| 4,837,378 | 6/1989 | Borgman | 424/81 |
| 5,266,329 | 11/1993 | Riley, Jr. | 424/430 |

FOREIGN PATENT DOCUMENTS

| 80363 | 11/1982 | Romania . |
| 82399 | 9/1983 | Romania . |
| 91013 | 5/1992 | Romania . |

OTHER PUBLICATIONS

Amsel R. et al. "Comparison of metronidazole, ampicillin, and amoxicillin for treatment of bacterial vaginosis (nonspecific vaginitis): possible explanation for the greater efficacy of metronidazole." In proceedings of the First U.S. Metronidazole Conference: pp. 225–242. Edited by Finegold S.M, George W.L., and Rolfe R.D. N.Y.: Biomedical Information Corporation (1982).
Balsdon M.J. et al., "Corynebacterium vaginale and vaginitis: a controlled trial of treatment." Lancet 1:501 (1980).
Barlett J.G. et al. Bacterial flora of the vagina: quantitative study. Rev. Infect. Dis. (Suppl 1) 6:S67–S72 (1984).
Bistoletti P. et al. "Comparison of oral and vaginal metronidazole therapy for nonspecific bacterial vaginosis." Gyencol. Obstet. Invest., 21:144–149 (1986).
Brenner W.E. et al., "Metronidazole–containing vaginal sponges for the treatment of bacterial vaginosis," Adv. Contracept. 2:363–369 (1986).
Centers for Disease Control. MMWR Supplement. "1985 STD treatment guidelines." vol. 34 (4S), Oct. 18, 1985.
Charles D. et al. Antimicrobial treatment of infectious vaginopathies. The Female Patient 10:25–42 (1985).
Davis B. et al. Analysis of metronidazole penetration into vaginal fluid by reversed–phased high–performance liquid chromatography. Am. J. Obstet. Gynec. 149:802–803 (1984).
Edelman D.A. et al., "Treatment of bacterial vaginosis with intravaginal sponges containing metronidazole," J. Reprod. Medicine 34(5):341–344 (1989).
Eschenbach D.A. et al. "A dose–duration study of metronidazole for the treatment of nonspecific vaginosis." Scand. J. Infect. Dis. (Suppl) 40:73–80 (1983).
Eschenbach D.A. et al. Diagnosis and clinical manifestations of bacterial vaginosis. Am. J. of Obstet. & Gynecol. 158:819–829 (1988).
Eschenbach D.A. et al. Prevalence of Hydrogen Peroxide–Producing Lactobacillus Species in Normal Women and Women Bacterial Vaginosis. J. Clin. Microbiology 27(2):251–256 (1989).
Fouts A.C. et al. Trichomonas vaginalis: reevaluation of its clinical presentation and laboratory diagnosis. J. Infect. Diseases 141:137–143 (1980).
Hager W.D. et al. Metronidazole for vaginal trichomoniasis. Seven–day vs Single–dose regimens. J.A.M.A. 244:1219–1220 (1980).
Hagstrom B. et al. "Comparison of two different regimens of metronidazole in the treatment of nonspecific vaginitis." Scand. J. Infect. Dis. (Suppl) 40:95–96 (1983).
Hill, L.V.H. et al. Vaginitis: current microbiological & clinical concepts. Can. Med. Assoc. J. 134:321–331 (1986).
Hillier S.L. et al., "Efficacy of Metronidazole–Containing Sponges for the Treatment of Bacterial Vaginosis." ICAAC Abstract No. 1056, p. 281 (1989).
Larsen B. et al. Vaginal microbial flora: composition and influence of host physiology. Ann. Intern. Med. 96:926–930 (1982).
Malouf M. et al., Dube J–L. "Treatment of Hemophilus vaginalis vaginitis." Obstet. Gynecol. 57(6):711–714 (1981).
Mardh P. et al. In vitro interactions between Lactobacilli and other microorganisms occurring in the vaginal flora. Scand. J. Infect. Dis, (Suppl) 40:47–51 (1983).
McCue J.D. Evaluation and management of vaginitis. Arch. Intern. Med. 149:565–568 (1989).
Mead P.B. et al. "Establishing bacterial vaginosis." Contemp. OB/GYN 27:186–203 (Feb. 1986).
Mollgaard B. et al. Vehicle effect on topical drug delivery. II. Concurrent skin transport of drugs and vehicle components. Acta Pharm. Succ. 20: 443–450 (1983).

(List continued on next page.)

*Primary Examiner*—Kimberly Jordan
*Attorney, Agent, or Firm*—Ted K. Ringsred

[57] ABSTRACT

A non-flowing composition and method for treatment of bacterial vaginosis are disclosed. An afflicted vagina is treated with a therapeutically effective but relatively low dose of metronidazole in a composition that includes a buffer system maintaining the composition at a pH value in the range of about 3.75 to about 4.25. The composition can also be used for prophylactic purposes.

49 Claims, 7 Drawing Sheets

OTHER PUBLICATIONS

Moorman C.N. et al. Impact of site release of vaginal pH buffer cream on introital colonization by gram–negative bacilli. J. Urology 147: 1576–1578 (1992).

Nielsen P.G. Treatment of rosacea with 1% metronidazole cream. A double–blind study. Br. J. Dermatol. 108: 327–332 (1983).

Nielsen P.G. A double–blind study of 1% metronidazole cream versus systemic oxytretracycline therapy for rosacea. Br. J. Dermatol. 109: 63–65 (1983).

Peeters M. et al. Adhesion of Garnerella vaginalis to vaginal epithelial cells: variables affecting adhesion and inhibition by metronidazole. Genitourin Med. 61:391–395 (1985).

Pheifer T.A. et al. "Nonspecific vaginitis: role of Haemophilus vaginalis and treatment with metronidazole." New Eng. J. Med. 298(26):1429–1434 (1978).

Purdon A. et al. An evaluation of single dose metronidazole treatment for Gardnerella vaginalis vaginitis. Obstet. Gynecol. 64:271 (1984).

Rein M.F. Vulvovaginitis and cervicitis, in Mandell G. L., Douglas R.G., Bennett T.E. (eds). Principles and Practice of Infectious Diseases, Edition 2, New York, John Wiley & Sons Inc., pp. 729–738 (1984).

Robie M.O. et al. Metronidazole use in obstretrics and gynecology: A review. Am. J. Obstet. Gynecol. 145: 865–879 (1983).

Skavin A. et al. Vaginal Lactobacilli inhibiting growth of Gardnerella vaginalis, mobiluncus and other bacterial species cultured from vaginal content of women with bacterial vaginosis. Acta. Path. Microbiol. Immunol. Scand., Section B, 94:399–403 (1986).

Staerfelt F. et al. A survey of genital infections in patients attending a clinic for sexually transmitted diseases. Scand. J Infect. Dis. 40:53–57 (1983).

Swedberg J. et al. "Comparison of single dose versus one week course of metronidazole for symptomatic bacterial vaginosis." JAMA, 258(8):1046–1049 (1985).

Totten P.A. et al. Selective differential human blood filagen media for isolation of Gardnerella vaginalis. J. Clin. Microbiol. 15:141–147 (1982).

Compendium (Canada): Flagyl (Metronidazole) (1987).

MetroGel-Vaginal®
(metronidazole vaginal gel)
0.75% Vaginal Gel

FIG. 4A

FOR INTRAVAGINAL USE ONLY
NOT FOR OPHTHALMIC, DERMAL, OR ORAL USE

DESCRIPTION:
METROGEL-VAGINAL is the intravaginal dosage form of the synthetic antibacterial agent, metronidazole, USP at a concentration of 0.75%. Metronidazole is a member of the imidazole class of antibacterial agents and is classified therapeutically as an anti-protozoal and anti-bacterial agent. Chemically, metronidazole is 2-methyl-5-nitroimidazole-1-ethanol. It has a chemical formula of $C_6H_9N_3O_3$, a molecular weight of 171.16, and has the following structure:

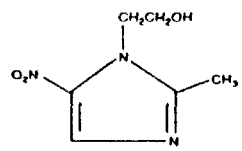

METROGEL-VAGINAL is a gelled, purified water solution, containing metronidazole at a concentration of 7.5 mg/g (0.75%). The gel is formulated at pH 4.0.' The gel also contains carbomer 934P, edetate disodium, methyl paraben, propyl paraben, propylene glycol, and sodium hydroxide.
Each applicator full of 5 grams of vaginal gel contains approximately 37.5 mg of metronidazole.

CLINICAL PHARMACOLOGY:
Normal Subjects:
Following a single, intravaginal 5-gram dose of metronidazole vaginal gel (equivalent to 37.5 mg of metronidazole) to 12 normal subjects, a mean maximum serum metronidazole concentration of 237 ng/mL was reported (range: 152 to 368 ng/mL). This is approximately 2% of the mean maximum serum metronidazole concentration reported in the same subjects administered a single, oral 500-mg dose of metronidazole (mean $C_{max}$ = 12,785 ng/mL, range: 10,013 to 17,400 ng/mL). These peak concentrations were obtained in 6 to 12 hours after dosing with metronidazole vaginal gel and 1 to 3 hours after dosing with oral metronidazole.

The extent of exposure [area under the curve (A.U.C.)] of metronidazole, when administered as a single intravaginal 5-gram dose of metronidazole vaginal gel (equivalent to 37.5 mg of metronidazole), was approximately 4% of the A.U.C. of a single oral 500-mg metronidazole dose (4977 ng-hr/mL and approximately 125,000 ng-hr/mL, respectively).

Dose adjusted comparisons of A.U.C.'s demonstrated that, on a mg to mg comparison basis, the absorption of metronidazole, when administered vaginally, was approximately half that of an equivalent oral dosage.

Patients with Bacterial Vaginosis:
Following single and multiple 5-gram doses of metronidazole vaginal gel to 4 patients with bacterial vaginosis, a mean maximum serum metronidazole concentration of 214 ng/mL on day 1 and 294 ng/mL (range: 228 to 349 ng/mL) on day five were reported. Steady state metronidazole serum concentrations following oral dosages of 400 to 500 mg B.I.D. have been reported to range from 6,000 to 20,000 ng/mL.

Microbiology:
The intracellular targets of action of metronidazole on anaerobes are largely unknown. The 5-nitro group of metronidazole is reduced by metabolically active anaerobes, and studies have demonstrated that the reduced form of the drug interacts with bacterial DNA. However, it is not clear whether interaction with DNA alone is an important component in the bactericidal action of metronidazole on anaerobic organisms.

Culture and sensitivity testing of bacteria are not routinely performed to establish the diagnosis of bacterial vaginosis. (See INDICATIONS AND USAGE.)

Standard methodology for the susceptibility testing of the potential bacterial vaginosis pathogens, *Gardnerella vaginalis*, *Mobiluncus* spp., and *Mycoplasma hominis*, has not been defined. Nonetheless, metronidazole is an antimicrobial agent active *in vitro* against most strains of the following organisms that have been reported to be associated with bacterial vaginosis:

*Bacteroides* spp
    *Gardnerella vaginalis*
    *Mobiluncus* spp.
    *Peptostreptococcus* spp.

INDICATIONS AND USAGE:
METROGEL-VAGINAL is indicated in the treatment of bacterial vaginosis (formerly referred to as *Haemophilus* vaginitis, *Gardnerella* vaginitis, nonspecific vaginitis, *Corynebacterium* vaginitis, or anaerobic vaginosis).

NOTE:     For purposes of this indication, a clinical diagnosis of bacterial vaginosis is usually defined by the presence of a homogeneous vaginal discharge that (a) has a pH of greater than 4.5, (b) emits a "fishy" amine odor when mixed with a 10% KOH solution, and (c) contains clue cells on microscopic examination. Gram's stain results consistent with a diagnosis of bacterial vaginosis include (a) markedly reduced or absent *Lactobacillus* morphology, (b) predominance of *Gardnerella* morphotype, and (c) absent or few white blood cells.

Other pathogens commonly associated with vulvovaginitis, e.g., *Trichomonas vaginalis*, *Chlamydia trachomatis*, *N. gonorrhoeae*, *Candida albicans*, and *Herpes simplex* virus should be ruled out.

FIG. 4B

CONTRAINDICATIONS:
METROGEL-VAGINAL is contraindicated in patients with a prior history of hypersensitivity to metronidazole, parabens, other ingredients of the formulation or other nitroimidazole derivatives.

WARNINGS:
Convulsive Seizures and Peripheral Neuropathy:
Convulsive seizures and peripheral neuropathy, the latter characterized mainly by numbness or paresthesia of an extremity, have been reported in patients treated with oral metronidazole. The appearance of abnormal neurologic signs demands the prompt discontinuation of metronidazole vaginal gel therapy. Metronidazole vaginal gel should be administered with caution to patients with central nervous system diseases.

Psychotic Reactions:
Psychotic reactions have been reported in alcoholic patients who were using oral metronidazole and disulfiram concurrently. Metronidazole vaginal gel should not be administered to patients who have taken disulfiram within the last two weeks.

PRECAUTIONS:
METROGEL-VAGINAL affords minimal peak serum levels and systemic exposure (A.U.C.'s) of metronidazole compared to 500 mg oral metronidazole dosing. Although these lower levels of exposure are less likely to produce the common reactions seen with oral metronidazole, the possibility of these and other reactions cannot be excluded presently. Data from well-controlled trials directly comparing metronidazole administered orally to metronidazole administered vaginally are not available.

General:
Patients with severe hepatic disease metabolize metronidazole slowly. This results in the accumulation of metronidazole and its metabolites in the plasma. Accordingly, for such patients, metronidazole vaginal gel should be administered cautiously.

Known or previously unrecognized vaginal candidiasis may present more prominent symptoms during therapy with metronidazole vaginal gel. Approximately 6% of patients treated with METROGEL-VAGINAL developed symptomatic *Candida* vaginitis during or immediately after therapy.

Disulfiram-like reaction to alcohol has been reported with oral metronidazole, thus the possibility of such a reaction occurring while on metronidazole vaginal gel therapy cannot be excluded.

METROGEL-VAGINAL contains ingredients that may cause burning and irritation of the eye. In the event of accidental contact with the eye, rinse the eye with copious amounts of cool tap water.

Information for the Patient:
The patient should be informed not to drink alcohol while being treated with metronidazole vaginal gel. While blood levels are significantly lower with METROGEL-VAGINAL than with usual doses of oral metronidazole, a possible interaction with alcohol cannot be excluded.

The patient should also be instructed not to engage in vaginal intercourse during treatment with this product.

Drug Interactions:
Oral metronidazole has been reported to potentiate the anticoagulant effect of warfarin and other coumarin anticoagulants, resulting in a prolongation of prothrombin time. This possible drug interaction should be considered when metronidazole vaginal gel is prescribed for patients on this type of anticoagulant therapy.

Drug/Laboratory test Interactions:
Metronidazole may interfere with certain types of determinations of serum chemistry values, such as aspartate aminotransferase (AST, SGOT), alanine aminotransferase (ALT, SGPT), lactate dehydrogenase (LDH) triglycerides, and glucose hexokinase. Values of zero may be observed. All of the assays in which interference has been reported involve enzymatic coupling of the assay to oxidation-reduction of nicotinamide-adenine dinucleotide (NAD+NADH). Interference is due to the similarity in absorbance peaks of NADH (340 nm) and metronidazole (322 nm) at pH 7.

Carcinogenesis, mutagenesis, impairment of fertility:

Metronidazole has shown evidence of carcinogenic activity in a number of studies involving chronic oral administration in mice and rats. Prominent among the effects in the mouse was the promotion of pulmonary tumorigenesis. This has been observed in all six reported studies in that species, including one study in which the animals were dosed on an intermittent schedule (administration during every fourth week only). At very high dose levels (approx. 500 mg/kg/day), there was a statistically significant increase in the incidence of malignant liver tumors in males. Also, the published results of one of the mouse studies indicate an increase in the incidence of malignant lymphomas as well as pulmonary neoplasms associated with lifetime feeding of the drug. All these effects are statistically significant. Several long-term oral dosing studies in the rat have been completed. There were statistically significant increases in the incidence of various neoplasms, particularly in mammary and hepatic tumors, among female rats administered metronidazole over those noted in the concurrent female control groups.

Two lifetime tumorigenicity studies in hamsters have been performed and reported to be negative. These studies have not been conducted with 0.75% metronidazole vaginal gel, which would result in significantly lower systemic blood levels than those obtained with oral formulations.

Although metronidazole has shown mutagenic activity in a number of *in vitro* assay systems, studies in mammals (*in vivo*) have failed to demonstrate a potential for genetic damage.

Fertility studies have been performed in mice up to six times the recommended human vaginal dose (based on mg/m$^2$) and have revealed no evidence of impaired fertility.

Pregnancy: Teratogenic Effects

Pregnancy Category B

There has been no experience to date with the use of METROGEL-VAGINAL in pregnant patients. Metronidazole crosses the placental barrier and enters the fetal circulation rapidly. No fetotoxicity or teratogenicity was observed when metronidazole was administered orally to pregnant mice at six times the recommended human vaginal dose (based on mg/m$^2$); however, in a single small study where the drug was administered intraperitoneally, some intrauterine deaths were observed. The relationship of these findings to the drug is unknown.

There are, however, no adequate and well-controlled studies in pregnant women. Because animal reproduction studies are not always predictive of human response, and because metronidazole is a carcinogen in rodents, this drug should be used during pregnancy only if clearly needed.

Nursing mothers:

Specific studies of metronidazole levels in human milk following intravaginally administered metronidazole have not been performed. However, metronidazole is secreted in human milk in concentrations similar to those found in plasma following oral administration of metronidazole.

Because of the potential for tumorigenicity shown for metronidazole in mouse and rat studies, a decision should be made whether to discontinue nursing or to discontinue the drug, taking into account the importance of the drug to the mother.

Pediatric use:

Safety and effectiveness in children have not been established.

ADVERSE REACTIONS:

Clinical Trials:

There were no deaths or serious adverse events in clinical trials involving 295 patients; however, approximately 1% of non-pregnant patients treated with METROGEL-VAGINAL discontinued therapy early due to drug-related adverse events. One patient discontinued therapy due to abdominal pain after 2 days of therapy and one patient discontinued therapy due to a severe headache after 5 doses. Similar headaches of uncertain cause had been reported in the past by this patient.

Medical events judged to be related, probably related, or possibly related to administration of METROGEL-VAGINAL were reported for 50/295 (17%) non-pregnant patients. Unless percentages are otherwise stipulated, the incidence of individual adverse reactions listed below was less than 1%:

*Genital tract:*
    Symptomatic *Candida* cervicitis/vaginitis (6.1%).
    Vaginal, perineal, or vulvar itching (1.4%).
    Urinary frequency, vaginal or vulvar burning or irritation, vaginal discharge (not *Candida*), and vulvar swelling.

*Gastrointestinal:*
    Cramps/pain (abdominal/uterine) (3.4%).
    Nausea (2.0%).
    Metallic or bad taste (1.7%).
    Constipation, decreased appetite, and diarrhea.

*Central Nervous System:*
    Dizziness, headache, and lightheadedness.

*Dermatologic:*
    Rash.

*Laboratory:*
    Increased/decreased white blood cell counts (1.7%).

Other metronidazole formulations:
Other effects that have been reported in association with the use of topical (dermal) formulations of metronidazole include skin irritation, transient skin erythema, and mild skin dryness and burning. None of these adverse events exceeded an incidence of 2% of patients.

METROGEL-VAGINAL affords minimal peak serum levels and systemic exposure (A.U.C.'s) of metronidazole compared to 500 mg oral metronidazole dosing. Although these lower levels of exposure are less likely to produce the common reactions seen with oral metronidazole, the possibility of these and other reactions cannot be excluded presently. Data from well-controlled trials directly comparing metronidazole administered orally to metronidazole administered vaginally are not available.

The following adverse reactions and altered laboratory tests have been reported with the oral or parenteral use of metronidazole:

*Cardiovascular:* Flattening of the T-wave may be seen in electrocardiographic tracings.

*Central Nervous System.* (See WARNINGS.) Headache, dizziness, syncope, ataxia, confusion, convulsive seizures, peripheral neuropathy, vertigo, incoordination, irritability, depression, weakness, insomnia.

*Gastrointestinal:* Abdominal discomfort; nausea; vomiting; diarrhea, an unpleasant metallic taste, anorexia; epigastric distress; abdominal cramping, constipation, "furry" tongue glossitis and stomatitis; pancreatitis; modification of taste of alcoholic beverages.

*Genitourinary:* Overgrowth of *Candida* in the vagina, dyspareunia, decreased libido, proctitis.

*Hematopoietic:* Reversible neutropenia, reversible thrombocytopenia.

*Hypersensitivity Reactions.* Urticaria; erythematous rash; flushing, nasal congestion; dryness of the mouth, vagina, or vulva; fever; pruritus, fleeting joint pains.

*Renal:* Dysuria, cystitis, polyuria, incontinence, a sense of pelvic pressure, darkened urine.

OVERDOSAGE:
There is no human experience with overdosage of metronidazole vaginal gel. Vaginally applied metronidazole, 0.75% could be absorbed in sufficient amounts to produce systemic effect. (See WARNINGS.)

DOSAGE AND ADMINISTRATION:
The recommended dose is one applicator full of METROGEL-VAGINAL (approximately 5 grams containing approximately 37.5 mg of metronidazole) intravaginally twice daily for 5 days. The medication should be applied once in the morning and once in the evening.

HOW SUPPLIED:
METROGEL-VAGINAL (metronidazole vaginal gel) 0.75% Vaginal Gel is supplied in a 70 gram aluminum tube and packaged with a 5 gram vaginal applicator. NDC number is 55326-200-25.
Store at controlled room temperature 15° to 30°C (59° to 86°F). Protect from freezing.
Caution: Federal law prohibits dispensing without a prescription.

This package insert issued 1/93.
Curatek Pharmaceuticals
Limited Partnership
1965 Pratt Blvd.
Elk Grove Village, IL 60007
Printed in U.S.A. © 1993 Curatek
126739-193

*Curatek*®

INTRAVAGINAL TREATMENT OF VAGINAL INFECTIONS WITH BUFFERED METRONIDAZOLE COMPOSITIONS

CROSS-REFERENCE TO RELATED APPLICATION

This application is a continuation of my U.S. patent application Ser. No. 295,242, filed on Aug. 24, 1994, now U.S. Pat. No. 5,536,743, which is a continuation-in-part of U.S. patent application Ser. No. 950,827, filed on Sep. 24, 1992, now abandoned, which is a continuation-in-part of my U.S. patent application Ser. No. 362,273, filed on Jun. 6, 1989, now abandoned, which, in turn, is a continuation-in-part of U.S. patent application Ser. No. 144,252, filed Jan. 15, 1988, now U.S. Pat. No. 4,837,378.

TECHNICAL FIELD

This invention contemplates a low dosage form and a method for intravaginal treatment of bacterial vaginosis with metronidazole formulations buffered to physiological vaginal pH.

BACKGROUND OF THE INVENTION

Bacterial vaginosis (BV) is associated with an increased volume of vaginal discharge which has a foul, fishy odor. Vaginal pH is elevated from the normal range (pH 3–4) to values $\geq$ pH 4.7. The odor and elevated pH are caused by a high level of amines, most notably trimethylamine, in the vagina. These amines are volatilized when the pH is raised, for example, as with addition of KOH or interaction with semen. The vaginal discharge is homogenous in appearance as opposed to the flocculent discharge seen in Candida vaginitis. In contrast to candidiasis and trichomoniasis, itching generally is not associated with BV. A microscopic examination of a wet mount of the vaginal discharge in BV reveals an absence of polymorphonuclear leukocytes (PMNs). In contrast, the presence of many PMNs in a vaginal discharge is indicative of trichomoniasis, gonorrhea, or chlamydial cervicitis.

The causative organism for BV is a matter of some controversy. Gardnerella vaginalis is usually implicated as the causative agent because it is isolated from 98% of women with BV. However, G. vaginalis is also recovered in smaller numbers as normal flora in the vagina of asymptomatic women in incidences as high as 68% (Totten et al, 1982).

In those conditions where Gardnerella is present in higher concentrations, there is a significant decrease in the numbers of Lactobacilli present compared to the normal vagina. The normal vaginal flora is composed predominantly of Lactobacillus species, with an average pH of 4.0 (Hill and Embil, 1986; Bartlett and Polk, 1984). This low pH fosters growth and maintenance of the acidophilic Lactobacilli (anaerobic and facultatively anaerobic Gram-positive bacilli) that dominate the normal flora in concentrations of $10^8$ to $10^9$ Lactobacilli per milliliter of vagina secretions (Larsen and Galask, 1982; Rein, 1985). While it is not known if a decrease in the Lactobacilli allows the Gardnerella to multiply, or if the increased numbers of Gardnerella actually inhibit the Lactobacilli, it is postulated that hydrogen peroxide production by certain Lactobacillus species represents a mechanism by which Lactobacilli regulate the growth of other organisms in the vagina (Eschenbach et al., 1989). In any event, if the predominant microorganism present in the wet mount is not Lactobacilli, then BV must be suspected.

There have been overgrowths of other microorganisms seen in BV. Mycoplasma hominis and anaerobic bacteria including Bacteroides, Peptococcus, and Mobiluncus are also highly associated with BV (Eschenbach et al, 1988). In BV, G. vaginalis and the anaerobes can be present in overgrowths 1000 to 100,000 times more frequently than normal. It is also not known if the anaerobes are a result of the decreased amounts of Lactobacilli, or if they are responsible for the decrease. These organisms are present, however, in concentrations that should be considered pathogenic (Mead et al, 1986).

Characteristically seen in the wet mount in BV are abnormal cells termed "clue cells." These clue cells are vaginal epithelial cells with such a heavy coating of bacteria surrounding them that their peripheral borders are obscured (Eschenbach et al. 1988).

Peeters and Piot (1985) developed an experimental model of the G. vaginalis adherence to vaginal epithelial cells forming "clue cells." Using this model they found that the optimum pH for adhesion in vitro was pH 5 to 6 (the vaginal pH of women with bacterial vaginosis) and adhesion was limited at pH 3 to 4 which is the normal pH of vaginal fluid in women without vaginosis. If the same is true in vivo, a rise in vaginal pH is possibly a prerequisite in the pathogenesis of BV and perhaps precedes the formation of the pathognomonic "clue cells."

The antibacterial activity of Lactobacilli against other microorganisms has been suggested (Mardh and Soltesy, 1983). Skavin and Sylwan (1986) found that Lactobacilli strains inhibited growth of bacterial strains implicated in and isolated from women with BV in in vitro cultures. The bacterial strains tested included Mobiluncus mulieris, Mobiluncus curtisii, G. vaqinalis, Peptococcus species, Peptococcus asaccharolvticus, Peptostrepotococcus anaerobius, Grampositive anaerobic coccus, and Bacteroides species. They also found that the lowest pH which would allow macroscopically visible growth of these bacterial strains ranged from pH 5.0 to 5.5. This data supports the importance of establishing and maintaining the presence of the Lactobacillus-dominated normal vaginal flora and the necessary pH environment for their growth and inhibition of other BV associated bacteria.

A clinical diagnosis of BV is made if three or more of the following four clinical criteria are present: (1) a homogenous discharge; (2) a pH$\geq$4.7; (3) a "fishy" amine odor upon the addition of 10% KOH to discharge; (4) presence of epithelial clue cells representing greater than or equal to 20% of vaginal epithelial cells (Eschenbach et al, 1988).

The efficacy of metronidazole in the treatment of BV is known. A marked effectiveness for metronidazole, given at 500 mg by mouth, twice daily for seven days has been demonstrated. Cure rates of 80–90% have repeatedly been reported since that time by the oral route of administration (Pheiffer et al., 1978; Balsdon et al., 1980; Eschenbach et al., 1983; Purdon et al., 1984; Charles et al., 1985; Swedberg et al., 1985; Malouf et al., 1981; Amsel et al., 1982; Hagstrom and Lindstedt, 1983; Mead et al., 1986). These studies employed the oral use of metronidazole in doses that ranged from 400 to 500 mg twice daily for three to seven days or 2 grams in a single dose. Heretofore, it has been generally accepted that the oral administration of metronidazole for five to seven days is the most effective way to treat DV; however, such a treatment for BV is not approved by the United States Food and Drug Administration (FDA). The Center for Disease Control recommends a dose of 500 mg of metronidazole given twice daily for seven days for treatment of bacterial vaginosis (CDC, 1985).

The adverse reactions from oral administration of metronidazole can be extensive, however. For metronidazole, the "Modern Drug Encyclopedia" [A. J. Lewis, Editor, pub. by Vocke Medical Books, New York, N.Y. (1979)], contains the following statement on metronidazole:

"Adverse Reactions: Nausea, headache, anorexia, vomiting, diarrhea, epigastric distress, abdominal cramping, constipation, a metallic, sharp and unpleasant taste, furry tongue, glossitis, stomatitis, leukopenia, dizziness, vertigo, incoordination, ataxia, convulsive seizures, numbness or paresthesia of extremities, fleeting joint pains, confusion, irritability, depression, insomnia, mild erythematous eruption, weakness, urticaria, flushing, dryness of the mouth, vagina or vulva, pruritus, dysuria, cystitis, sense of pelvic pressure, dyspareunia, fever, polyuria, incontinence, decrease of libido, nasal congestion, proctitis, pyuria, and rarely, an unexplained darkening in the color of the urine have been reported. Flattening of the T wave may be seen in electrocardiographic tracings."

The need for providing safe and effective treatment for BV (without, for example, the side effects associated with the oral usage of metronidazole) assumes a more acute and pressing status when epidemiological trends and possible sequelae of a serious nature are given consideration. For example, vaginal infection with *G. vaginalis*, has been associated with possible sequelae, such as pelvic inflammatory disease, endometritis, and premature labor (Mead et al., 1986) that have an attendant, significant morbidity profile. Although there is no direct evidence linking BV with these conditions, it is not unreasonable to assume that an overgrowth of 10,000 to 100,000 anaerobic organisms in the vagina may result in certain genital diseases (Mead et al, 1986). Moreover, in the last decade there has been a tendency towards a reduction in gonorrhea and trichomoniasis while, during the same time span, there has been an increase in the so called "non-specific genital disease" (Staerfelt et al, 1983). Further, BV may account for significantly more total vaginitis patients than either Candida or trichomoniasis (Mead et al, 1986).

Since BV is a localized problem, intravaginal application of metronidazole should in principle be clinically effective. Moreover, since in intravaginal application, unaffected organ systems would be subjected to significantly lower or non-detectable levels of metronidazole, its side effects would be therefore minimized or eliminated.

A desirable treatment for BV would be an intravaginal composition that delivers a minimum effective dose of metronidazole while it simultaneously adjusts and maintains the vaginal pH at about the normal physiological range while promoting the growth of Lactobacillus species that produce hydrogen peroxides and controlling the overgrowth by pathogens.

Intravaginal metronidazole therapy for BV has been studied (Bistoletti et al., 1986). The authors compared oral treatment which consisted of 400 mg of metronidazole in the morning and evening for seven days to vaginal treatment consisting of the application of a vaginal insert containing 500 mg of the drug every evening for seven days. Thus, the total dose given was 5.6 g in the oral, and 3.5 g in the vaginal, treatment groups. The findings in the 38 patients who completed the study showed a cure rate, at four weeks after initiation of therapy, to be 15 out of 19 (79%) for the vaginal treatment group and 14 out of 19 (74%) after oral treatment. Cure was based on assessment of pH, vaginal discharge, the 10% KOH amine test, and examination of a wet smear for clue cells. These same authors also reported that lactate-producing microorganisms (Lactobacilli and aerobic Streptococci) were found more frequently after vaginal than after oral treatment and speculated that this difference may be due to the higher local concentration of the drug achieved by intravaginal administration. In this regard, a low concentration of metronidazole has been found in the vaginal fluid after a single oral dose of 2 grams metronidazole (Davis et al., 1984). These authors concluded that topical administration of metronidazole might be more effective in re-establishing the normal microflora in the vagina. No side effects were reported related to the intravaginal use of metronidazole as the 500 mg insert. Although this study showed effectiveness of vaginally administered metronidazole, these researchers still used a relatively high dose (3.5 grams) and made no attempt to adjust and control vaginal pH. Moreover, these authors did not recognize the criticality of low pH for selectively promoting the growth of hydrogen peroxide producing Lactobacillus species.

Intravaginal sponges containing metronidazole also have been described. Brenner et al., Adv. Contracept. 2:363–368 (1986), describe the use of metronidazole and nonoxynol-9 containing sponges where each sponge contains 250 milligrams of metronidazole and 650 of nonoxynol-9 and estimate that about 160 milligrams of metronidazole in each sponge is released over a 24-hour use period.

Because of low water solubility of metronidazole, various oil-based metronidazole compositions have been developed, which are generally either creams (oil in water emulsions) or ointments (petroleum jelly based compositions) with metronidazole being dissolved/suspended in the oil/water phases.

Romanian Patent No. 80,363, published Nov. 30, 1982 (reported also at C.A. 101:116743c), describes a vaginal gel with antibiotic and anti-inflammatory activity. This gel comprises metronidazole, nystatin with other antibacterials selected from nitrofural, chloramphenicol, and tetracycline and camazulene or hexoestrol acetate incorporated into Carbopol 940™, an aqueous gel-forming polyacrylic acid polymer available from B. F. Goodrich, Cincinnati, Ohio.

Such gel formulation suffers from the disadvantage that it includes, in addition to metronidazole, various active antibiotic, antimicrobial and antimycotic agents. Such gel formulation then operates intravaginally on a broad spectrum "shot gun" basis to destroy not only the harmful bacteria associated with "vaginitis," but also the desirable bacteria, such as the Lactobacilli and other lactate-producing organisms (e.g., aerobic Streptococci) that are present in the normal vagina. In addition, the Romanian patent teaches a gel formulation for intravaginal use which is formulated at a pH of 6 to 6.5. Hence, use of such a vaginal gel formulation is open to question from the standpoint of being a safe treatment for BV since it leaves the treated vagina in an abnormal condition where reinfection or infection by other opportunistic microorganisms are possible sequelae.

A known commercial vaginal formulation of metronidazole currently on the international market for use as a trichomonacide, but not in the United States, is produced by Rhone-Poulenc Pharma Inc. of Montreal, P.Q., Canada. This formulation is a cream which contains 500 mg of metronidazole per application (5 grams). The recommended dose for trichomoniasis is one application once or twice daily for 10 to 20 days. Therefore, the total dose recommended ranges between 5 grams and 20 grams of metronidazole. The pH value of this formulation was tested by an independent laboratory to be pH 6.1.

So far as known, no one has heretofore formulated or used metronidazole for intravaginal treatment of bacterial vaginosis at about the physiological pH of the vagina (that is, a pH in the range of about 3 to about 4.25). In addition, no one has successfully treated BV with less than multiple gram doses of metronidazole.

The need for a safe and effective treatment for bacterial vaginosis which can eliminate the invading organisms at a low, safe dose and provide the necessary vaginal environment for growth and maintenance of lactate-producing organisms without overgrowth of potential pathogens remains.

SUMMARY OF THE INVENTION

The present invention provides a safe and effective, relatively low-dose treatment of a human vagina which is afflicted with BV. The invention also obviates the need for oral administration of metronidazole for BV, which administration can lead to undesirable side effects, as above reviewed.

A method aspect of this invention comprises introducing into such an afflicted vagina a therapeutically effective amount of metronidazole in a buffered, non-flowing pharmaceutical composition having a low, acidic pH value, preferably in the range of about 3.75 to about 4.25. The present method not only provides an effective relatively low-dose treatment of BV, but also promotes the beneficial and effective re-establishment of the normal vaginal microflora, such as Lactobacilli, especially the hydrogen peroxide producing species. Thus, for example, the inventive method provides not only an effective BV treatment, but also a safe treatment since it leaves the treated vagina in a substantially normal condition able to cope with, and resist, future microorganism infections. So far as now known, no other existing BV treatment offers such an advantage. The present treatment contemplates administration of the composition at least once a day for a time period of at least one day and up to ten days, preferably three to ten days.

In accordance with another aspect of the present invention, a class of buffered metronidazole compositions is provided which is particularly well suited for the practice of such method. Buffered formulations of this class not only have the ability to control and eliminate, at surprisingly low dosages, the anaerobic bacteria population causing BV, but also have the ability to adjust and maintain the vaginal environment at about the normal physiological pH. Thus, such compositions provide the necessary environment for the restoration of favorable bacterial flora while delivering a relatively low, but therapeutic amount of metronidazole.

Yet another aspect of the present invention entails the prevention of bacterial vaginosis in susceptible patients by the intravaginal administration of a prophylactic amount of the buffered metronidazole compositions described in greater detail hereinbelow.

The present compositions contain metronidazole as the sole active ingredient at a concentration of at least about 0.1 weight percent, based on the weight of the composition, together with a buffer system in a physiologically tolerable medium. The buffer system is capable of providing a buffered pH value in the range of about 3.75 to about 4.25.

Presently preferred such compositions are aqueous gels that incorporate metronidazole, a gelled hydrophilic and water-dispersible polyacrylic acid polymer having free carboxylic acid groups, a buffer system, and an aqueous solvent for metronidazole and the buffer system.

A prolonged, substantially uniform and controlled release rate of metronidazole from the treating composition in the vaginal canal is provided by these compositions.

In a presently preferred mode of practicing this invention, a composition containing metronidazole as the sole active ingredient together with a buffer system capable of providing a buffered pH value in the range of about 3.75 to 4.25 is administered intravaginally to a patient afflicted with BV at a surprisingly low total dose of about 375 milligrams of metronidazole or less, administered in unit doses of at least about 20 milligrams each one to three times daily over a period of at least one day and up to ten days, preferably for three to ten days. This dose is substantially less than that previously employed for effective therapy with metronidazole. This reduced dose rate is believed to be related to the difference in pH adjustment and maintenance.

Numerous other advantages and features of the present invention will become readily apparent from the following description of the preferred embodiments of the invention, the accompanying examples, the drawings, and the appended claims.

BRIEF DESCRIPTION OF THE DRAWINGS

In the figures forming a part of the disclosure:

FIG. 4 is a copy of both sides of the package insert included with the article of manufacture.

DESCRIPTION OF PREFERRED EMBODIMENTS

While this invention is susceptible to embodiment in many different forms, preferred embodiments of the invention are described hereinbelow in detail. It should be understood, however, that the present disclosure and the embodiments described herein are to be considered as exemplifications of the principles of this invention and are not intended to limit the invention.

The present invention is practiced therapeutically by introducing into such an afflicted vagina a therapeutically effective amount of a buffered formulation of metronidazole, such as hereinbelow described and exemplified. Moreover, the present invention also contemplates the use of the hereindescribed metronidazole compositions for preventing bacterial vaginosis in human female patients that are susceptible to it. To that end, a prophylactic amount of a non-flowing, viscid composition which contains metronidazole as the sole active ingredient and has a pH value in the range of about 3.75 to about 4.25 is administered intravaginally chronically or for a time period while the susceptibility exists.

The term "vagina" as used herein is intended to be inclusive of the vaginal region generally, including also the vulva and the cervix. Also, the term "afflicted vagina" as used herein is intended to be inclusive of bacterial vaginosis (BV).

The quantity of metronidazole introduced intravaginally as a single or unit dose can vary widely, depending upon many variables, such as the age and physical condition of the patient, the extent of the patient's affliction, the frequency of administration, the need for prophylaxis, and the like.

The term "unit dose" or "unit dosage form" as used in the specification and claims refers to physically discrete units of such composition suitable for use as unitary dosages by human female subjects. Each unit contains a predetermined quantity of metronidazole calculated to produce the desired therapeutic effect in association with the required pharmaceutical vehicle. The exact novel unit dosage form(s) of the invention to be used for any given patient is/are dictated by, and directly dependent on (a) the unique characteristics of the metronidazole compositions and the particular therapeutic effects to be achieved, and (b) the characteristics, especially the release rate of metronidazole from the particular composition contemplated for the intended therapeutic use, as disclosed in detail in the present specification, these being features of the present invention.

Figure 3:
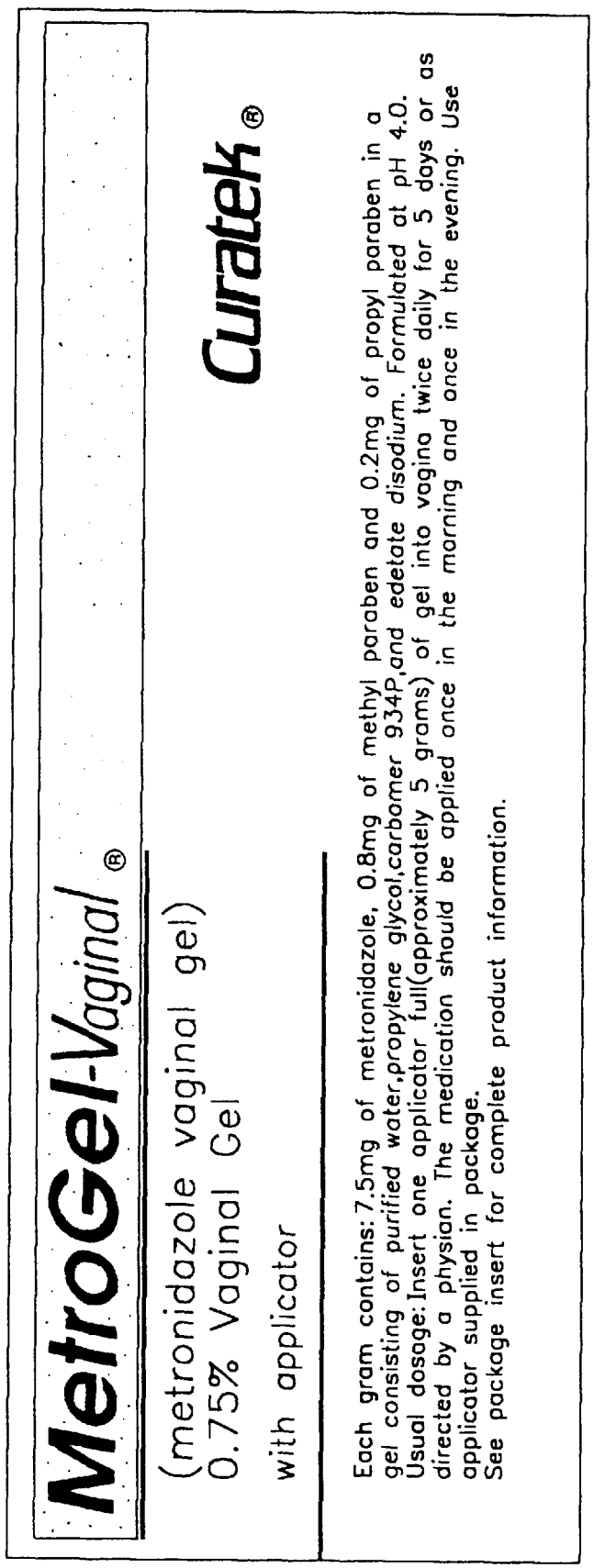
FIG. 3 is a depiction of an article of manufacture embodying the present invention.

An article of manufacture embodying the present invention is shown in FIG. 3 and includes a packaging material and contained therein a pharmaceutical agent consisting essentially of metronidazole and the aforementioned buffer system in a physiologically tolerable medium. The packaging material includes a label which indicates that the pharmaceutical agent can be used for ameliorating the symptoms of bacterial vaginosis, preferably by administering about 37.5 milligrams of metronidazole in an aqueous gel twice daily for five days. Both sides of the package insert are shown in FIG. 4.

Any convenient non-flowing, i.e., self-supporting and viscid, such as gel, paste, cream, and the like, unit dose form can be employed in practicing this invention. A presently preferred technique is to extrude a non-flowing composition, such as a gel composition, through a tubular applicator from a storage vessel, such as a syringe, squeezable tube, or the like, into the afflicted vagina. The volume of gel composition so contained within a single such vessel is conveniently and preferably selected so as to constitute a single dose, or two doses, or the like, so as to facilitate administration of a desired controlled dose to a patient. The storage vessel is initially sealed, but is opened at the time of use. If more than a single dose is present, the vessel is preferably resealable by a suitable closure means.

Another presently preferred technique is to employ a single use packet (such as a small envelope-like structure, or the like) containing an intended single unit dose. The packet is initially sealed, but is opened at the time of use by tearing, cutting, or the like at a desired or planned location in the packet after which the packet is manually squeezed so that the contents are directly administrable as desired.

The quantity of metronidazole contained in a unit dose is generally at least about 20 milligrams (mg), and is not more than about 100 mg. A typical and presently preferred unit dose in a gel vehicle is in the range of about 20 to about 40 mg, most preferably about 37.5 mg, per dose.

Such a quantity can be administered one to three times daily (that is, at spaced intervals in a 24 hour period) in a single day or over a period of up to ten days. The total daily dose thus delivered can range from about 20 to about 100 mg. In a gel form of the composition, a daily dose in the range of about 30 to about 80 mg usually is sufficient. The usual total dose during the course of therapy for compositions of the present invention is in the range of about 100 mg to about 375 mg. A presently preferred administration procedure is to employ a unit dose of 5 grams of gel (delivering a dose of 37.5 mg of metronidazole) administered once or twice daily for a period of about five days, thereby to deliver a total dose in the range of about 185 mg to about 375 mg. Those skilled in the art will appreciate that the foregoing dose levels are provided illustratively, and that higher and lower dose levels can be employed without departing from the spirit and scope of the present invention.

Such doses are significantly lower than the comparable 7 gram dose (500 mg b.i.d. employed for 7 days, the standard BV dosage) as currently utilized and recommended by CDC. The low daily dose of the particularly preferred gel composition directly applied to the site of activity decreases the risks of dose related side effects and potential systemic activity. The effectiveness of this novel, low dose therapy is believed to be related to the combination of site specificity, controlled release, pH adjustment, control of vaginal environment, and provision for reestablishment of necessary normal vaginal flora, i.e., lactate producing microorganisms and hydrogen-peroxide producing microorganisms.

For prophylactic purposes, the amount of metronidazole administered is in the range of about 20 milligrams to about 80 milligrams, more preferably in the range of about 30 to about 40 milligrams per dose. These prophylactic amounts can be introduced intravaginally as a single dose or more than one dose, as desired, preferably twice a week on non-consecutive days.

The active ingredient in the present composition is 1-(2-hydroxyethyl)-2-methyl-5-nitroimidazole (metronidazole). This drug is described in U.S. Pat. No. 2,944,061 to Jacob et al., and is commercially available.

The term "metronidazole" as used in this specification and claims includes not only 1-(2-hydroxyethyl)-2-methyl-5-nitroimidazole, but also those analogs and derivatives of metronidazole (salts, esters, etc.) which are soluble in the aqueous or oil phases of the compositions described herein and which exhibit therapeutic activity when applied as taught by the present invention. A physiologically tolerable medium is utilized as the delivery vehicle for metronidazole.

The term "physiologically tolerable medium" as used herein refers to one or more viscous-to-solid materials, i.e., of non-flowing consistency, which are non-irritating to the vaginal region. While a given such medium in a presently contemplated composition can be comprised of a single material, a plurality of components can comprise such a medium as well. Examples of components include water, oil, surfactants, preservatives, penetration enhancers, preservatives, and the like, such as hereinbelow described and illustrated. For purposes of avoiding problems of pooling and running, the physiologically tolerable medium is preferably characterized by a viscosity at ambient conditions (e.g., 25° C., 760 mm Hg) with said metronidazole and also said buffer system dissolved and/or dispersed therein which is at least sufficient to maintain a product composition of this invention in a non-flowing state.

The term "buffer system" or "buffer" as used herein has reference to a solute agent or agents which, when in water solution, stabilize such solution against a major change in pH (or hydrogen ion concentration) when acids or bases are added thereto. Solute agent or agents which are thus responsible for a resistance to change in pH from a starting buffered pH value in the range above indicated are well known.

For example, a pH of 4.024 can be obtained with a solution of 0.05M acid potassium phthalate. Similarly, a pH value of about 4.0 can be achieved with an acetic acid-sodium acetate buffer. Also, a pH value of about 4.0 can be achieved with, for example, 50 ml of 0.1 molar potassium hydrogen phthalate plus about 0.1 ml of 0.1M HCl, and a pH value of about 4.1 can be achieved with, for example, 50 ml of 0.1M potassium hydrogen phthalate plus about 1.3 ml of 0.1M NaOH. Various other buffers for achieving the desired pH values are also available, for example, DL-valine (pH 4.0), and the like. Virtually any pharmaceutically acceptable buffer system can be used which will achieve a pH in the range indicated for topical applications.

Buffered formulations of metronidazole suitable for vaginal introduction in accord with the present invention and suitable for achieving the desired therapeutic action and desired physiological pH of the vagina can be in any convenient non-flowing form, such as suspensions; emulsions; clear and opaque gels; semisolid systems, including ointments, pastes, oil-in-water (o/w) creams, semisolid emulsions with solid internal phases, semisolid emulsions with fluid internal phases; vaginal suppositories; tablets (inserts); and the like.

Buffered metronidazole composition vehicles suitable for use in practicing this invention may be classified as follows:

1. Oleaginous compositional bases or ointments that are all oil, e.g., petrolatum and mineral oil systems
2. Absorption compositional bases
    a. Anhydrous oleaginous systems which absorb water
    b. Water-in-oil (w/o) emulsion systems, e.g., aquaphor
3. Emulsion compositional bases of the water-in-oil (w/o) type
4. Emulsion compositional bases of the oil-in-water type (o/w)
5. Anhydrous water soluble compositional bases
6. Suppositories/inserts Each of the above indicated drug delivery vehicles is known in the art; however, for exemplary purposes of preparing compositions for use in the practice of this invention, the following detailed descriptions are provided:

1. Oleaginous Bases or Ointments:

This class of formulations comprises metronidazole and hydrocarbon-based semisolids containing dissolved and/or suspended bacteriostats/preservatives and a buffer system. The petrolatum component in these bases can be any paraffin ranging in viscosity from mineral oil employing incorporated isobutylene, colloidal silica, or stearate salts to paraffin waxes. White and yellow petrolatum are examples of such systems. Bases of this class can be made by incorporating high-melting waxes into a fluid mineral oil via fusion or by incorporation of polyethylene into mineral oil at elevated temperature. Polysiloxanes (also known as silicones) are suitable for use in these bases and typically have a viscosity in the range of about 0.5 to $10^6$ centistokes. The organic entities attached to the polysiloxane are preferably lower molecular weight hydrocarbon moieties having from 1 to 8 carbons each, such as lower alkyl, lower alkenyl, phenyl and alkyl substituted phenyl, and phenyl(lower)alkyl, such as benzyl. In such a moiety, each lower alkyl or alkenyl group preferably has 1 to 3 carbons inclusive, such as in a dimethylsiloxane polymer. A specific formulation for an oleaginous system is illustrated in the examples below.

2. Absorption Bases:

Absorption bases used for these buffered formulations can be oleaginous systems which contain, in addition to metronidazole, ingredients with the capacity to emulsify a significant quantity of water. Water-in-oil (w/o) emulsions can be formed wherein the external phase is oleaginous in character. Preservatives/bacteriostats, such as the parabens, buffer systems, etc. can be incorporated into these bases as emulsified aqueous solutions together with the active ingredient. Diverse additives are conveniently used as the emulsifier, and these include, but are not limited to, cholesterol, lanolin (which contains cholesterol and cholesterol esters and other emulsifiers), lanolin derivatives, beeswax, fatty alcohols, wool wax alcohols, low HLB (hydrophobe/lipophobe balance) emulsifiers, and assorted ionic and nonionic surfactants, singularly or in combination.

3. Water-In-Oil (W/O) Emulsion Bases:

These formulations can be an expansion of the general class of absorption bases which are liquids or creams. They can be prepared by taking a mixture of metronidazole with oil phase ingredients, bacteriostats/preservatives and buffer salts which are dissolved or suspended therein and to which water has been added to form a water-in-oil emulsion.

Compositions shown in the examples below are provided as being exemplary of these systems, but those skilled in the art will appreciate that substitutions, additions, and/or omissions of the specified components can be made. A listing of alternate components that could be incorporated in these examples is provided hereinbelow.

4. Oil-In-Water (O/W) Emulsion Bases:

These systems are semisolid emulsions, microemulsions, or foam emulsion systems containing metronidazole. Usually such a system has a "creamy white" appearance. Typically, the internal oil phase is in the range in percentage composition of about 10% to about 40% oil by weight and the external phase may contain 80% or more water. The oleaginous phase may contain, but is not limited to, long-chain alcohols (cetyl, stearyl), long-chain esters (myristates, palmitates, stearates), long-chain acids (palmitic, stearic), vegetable and animal oils and assorted waxes. These can be made with anionic, cationic, nonionic or amphoteric surfactants, or with combinations especially of the nonionic surfactants. The examples below are exemplary of these systems, but those skilled in the art will appreciate that substitutions and additions or omissions of the specified components could be made by one who is skilled in the art. A listing of alternate components is provided below.

5. Anhydrous Water Soluble Bases:

These systems include solutions or suspensions of metronidazole and the desired buffer system in glycols, such as glycerin, polyethylene glycol, propylene glycol which are thickened with hydroxypropyl cellulose.

The examples below are provided as being illustrative of these systems. Those skilled in the art will appreciate that substitutions, additions and/or omissions of the specified components can be made. A listing of alternate components that could be incorporated in these composition examples is provided below.

6. Vaginal Inserts and Suppositories:

Suppositories containing metronidazole can be, for example, oleaginous in nature which melt at body temperature, or polyethylene glycol-based which dissolve in the vaginal fluids. Additional bases for suppositories are glycerin and glycerinated gelatin.

Metronidazole can be readily formulated into buffered gels made with gelling agents. Some examples of these gelling agents are:

Cellulosics—Methyl cellulose, carboxymethyl cellulose, hydroxyethyl cellulose, and hydroxypropyl cellulose Cationic Polymers—"Polyquaternium-10", a polymeric quaternary ammonium salt of hydroxyethyl cellulose reacted with a trimethyl ammonium-substituted epoxide, and the like Polyoxyalkylenes and derivatives thereof— polyoxyethylene/polyoxypropylene esters of lanolin Carboxyvinyl polymers—cross-linked acrylic acid polymers, e.g., those commercially available from B. F. Goodrich Co., Akron, Ohio, under the designation CARBOPOL™

The examples below exemplify these systems, but those skilled in the art will appreciate that substitutions, additions and/or omissions of the specified components can be made. A listing below exemplifies alternate components that could be incorporated in these examples:

Surfactants

As above indicated, the buffered formulations of this invention can contain one or more surfactants. Suitable surfactants include anionic, cationic, amphoteric and non-ionic surfactants which are pharmaceutically acceptable in topical applications. Any one or more surfactants having the above characteristics can be used. Representative examples of suitable surfactants which can be used in the formulations of this invention are described in Martin and Cook, *Remington's Practice of Pharmacy*, 12th edition, 1961, pp. 219–226, R. G. Harry, *Cosmetics: Their Principles and Practices*, (1965), pp. 396–398 and 413–417, and E. Sagarin, *Cosmetics Science and Technology*, (1957), pp. 328–333, 1060–1063 and 1254, which publications are herein incorporated by reference. Representative surfactants which are suitable include:

A. Anionic Agents

1. Sodium, potassium and ammonium soaps derived from fatty acids having from 10 to 22 carbon atoms; and polyvalent metal (magnesium, calcium, zinc, aluminum and lead) soaps derived from fatty acids having from 10 to 22 carbons.

2. Amine soaps derived from fatty acids having from 10 to 22 carbons and primary, secondary and tertiary amines, such as monoethanolamine, diethanolamine and triethanolamine, and cyclic amines, such as morpholine. An examples is triethanolamine stearate, or the like.

3. Rosin soaps, such as sodium salts of rosin acids, e.g., abietic acid.

4. Alkali metal salts of sulfate compounds which can be represented by the formula $ROSO_3H$ wherein the R group represents an organic moiety, such as, for example, a fatty alcohol residue having up to 22 carbons. Examples include sodium lauryl sulfate, sodium cetyl sulfate, sodium monolauryl glyceryl sulfate, an oil such as sulfated castor, olive, teaseed, neat's foot cottonseed, rape seed, corn and rice, oil, and the like.

5. Alkali metal salts of sulfonated compounds which can be represented by the formula $RSO_3H$ wherein the R group can have from 8 to 22 carbons. These include alkane sulfonates, such as dioctyl sodium sulfosuccinate, oxyethylated alkylaryl sulfate, alkyl aromatic sulfonates such as sodium isopropylnaphthalenesulfonate, sodium dodecylbenzenesulfonate, sodium sulfonaphthylstearate, and the like.

B. Cationic Agents

1. Amine salts (e.g., hydrochlorides and acetates) derived from straight chain fatty amines having from 8 to 18 carbons. An example is octodecylamine hydrochloride, and the like.

2. Quaternary ammonium salts formed by alkylation of fatty amines with methyl chloride, dimethylsulfate, benzylchloride, and the like. These compounds can be represented by the formula $[RR'R''R'''N]Y$ wherein each of R, R', R'', R''' is a long chain aliphatic group of from 8 to 22 carbons or a fatty acid amide residue; a short aliphatic group, such as methyl, ethyl, or propyl, an aromatic group, such as a phenyl or benzyl radical; or a heterocyclic group, such as pyridine or piperidine residue; and Y represents an inorganic or lower organic cation, such as chloride, bromide or acetate radical. Examples include triethanolamine stearate, cetyl trimethyl ammonium bromide, benzalkoniumchloride, and the like.

C. Nonionic Agents

1. Ethers, such as condensation products of alkylphenols with from 6 to 20 moles of ethylene oxide, such phenols being monoalkylated, dialkylated or polyalkylated with alkyl side chains having from 5 to 18 carbons each, and the corresponding naphthalene or diphenyl compounds. Examples include polyoxyethylene, polyoxyethylene-polyoxypropylene copolymers, and the like.

2. Esters, such as compounds which can be represented by the formula RCOOR' wherein R is a long hydrocarbon chain derived from a fatty acid having from 12 to 22 carbons, and R' is derived from a polyhydric alcohol. Examples include glyceryl monostearate, diethylene glycol monolaurate, sorbitan fatty acid esters derived, for example, from lauric, palmitic, stearic and/or oleic acids, and the like.

3. Ether-esters wherein polyoxyethylene chains are found with an unreacted hydroxy group of esters of fatty acids and polyhydric alcohols.

4. Fatty acid amides, such as lauroyl diethanolamide and the like.

D. Ampholytic Agents

1. Surfactants, such as those having amino and carboxy groups. Examples include dodecyl Balanine, imidazoline derivatives such as the so-called "Miranols", and the like.

2. Surfactants containing amino and sulfuric acid or sulfonic acid groups formed by condensing an alkane-sulfonamide with formaldehyde and methyltaurine.

Suitable representative surfactants from the above indicated four general classes include sorbitan trioleate, sorbitan tristearate, sorbitan sesquioleate, glycerol monostearate, sorbitan monostearate, sorbitan monopalmitate, sorbitan monolaurate, polyoxyethylene lauryl ether, polyethylene glycol 400 monostearate, triethanolamine oleate, polyoxyethylene glycol 400 monolaurate, polyoxyethylene sorbitan monostearate, polyoxyethylenesorbitan monooleate, polyoxyethylene sorbitan monolaurate, sodium oleate, potassium oleate, sodium lauryl sulfate, lauroyl imidazoline, sodium dodecylbenzene sulfonate, sodium monoglyceride sulfate, sodium alkaralkyl polyglycol sulfate, sodium oleyl taurate, sodium dioctyl sulfosuccinate, lauryl polyglycol, ether, sodium dibutylnaphthalenesulfonate, alkyl phenol polyglycol ether, sorbitan monolaurate polyglycol ether, sulfonated castor oil, tall oil polyglycol ester, alkyl dimethyl benzylammonium chloride, alkyl naphthalene pyridinium chloride, cetyl dimethyl ethylammonium bromide, alkyl dimethyl chlorobenzylammonium chloride, dibutyl phenyl phenol sulfonate, ester of colaminoethylformyl methyl pyridinium chloride, sulfonated methyl oleylamide, sorbitan monolaurate polyglycol ether, polyglycol oleate, sodium lauryl sulfoacetate, sodium 2-ethylhexanol sulfate, sodium 7-ethyl-2-methylundecanol-4 sulfate, sodium 3,9-diethyltridecanol-6 sulfate, sodium lauryl and myristyl collamide sulfonate and N-(sodium sulfoethyl) oleamide, and the like.

Preservatives

As above indicated, the buffered compositions of this invention can contain suitable bacterostats, preservatives, inhibitors, or the like, such as methyl, ethyl, propyl, and butyl esters of parahydroxybenzoic acid, propyl gallate, sorbic acid and its sodium and potassium salts, propionic acid and its calcium and sodium salts, "Dioxin" (6-acetoxy-2,4-dimethyl-m-dioxane), "Bronopol" (2-bromo-2-nitropropane-1,3-diol) and salicylanilides such as disbromosalicylanilide, tribromosalicylamilides, "Cinaryl" 100 and 200 or "Dowicil" 100 and 200 (Cis isomer of 1-(3-chloroallyl-3,5,7-triaza-1-azanidadamantane chloride), hexachlorophene, sodium benzoate, citric acid, ethylene diaminetetraacetic acid and its alkali metal and alkaline earth metal salts, butyl hydroxyanisol, butyl hydroxytoluene, phenolic compounds such as chloro- and bromocresols and chloro- and bromo-oxylenols, quaternary ammonium compounds like benzalkonium chloride, aromatic alcohols such as phenylethyl alcohol, benzyl alcohol, etc., chlorobutanol, quinoline derivatives such as iodochlorhydroxyquinolin, and the like.

Hydrophilic and Hydrophobic Thickeners
(Suspending, gelling, or viscosity inducing agents)

Suitable thickeners which may be used in the composition of this invention include colloidal alumina, colloidal silica, alginic acid and derivatives thereof, "Carbopols" (carboxyvinyl polymers), cellulose derivatives, such as "Klucel" (cellulose ethers), Methocel (methyl cellulose), "Natrosol" (hydroxyethyl cellulose), sodium carboxymethyl cellulose, gelatin, natural gums, such as agar, tragacanth, acacia gum, guar gum, stearates, isobutylene, waxes, carrageen, and the like, egg yolk, lecithin, pectin, thixcin, resins like ethyleneoxide polymers, such as the so called polyoxes, and the like.

Other Adjuvants/Cosolvents

Other adjuvants which can be incorporated into a composition of this invention includes waxes, such as beeswax, spermaceti, paraffin waxes, and fatty acids, alcohols and amides having from 10 to 22 carbons, and the like.

Monohydric alcohols can be used, such as those having from 1 to 22 carbons per molecule, such as methanol, ethanol, propanol, isopropanol, butanol, hexanol, cetyl alcohol, stearyl alcohol, and the like.

Dihydric and polyhydric alcohols can be used, such as those having from 2 to 22 carbons per molecule, such as propylene glycol, glycerin, hexanetriols, such as 1,2,6-hexanetriol, sorbitol, 1,3-butanediol, 2,3-butanediol, and the like.

Polyethylene glycols and polypropylene glycols can be used, such as those having molecular weight in the range of about 100 to about 20,000.

Esters of aliphatic monobasic and dibasic acids can be used, such as those having from 2 to 22 carbons per molecule, with (a) monohydric alcohols having from 1 to 20 carbons per molecule, (b) di- and polyhydric alcohols having from 2 to 20 carbons per molecule, and (c) sugar alcohols. Examples include isopropyl myristate, myristyl myristate, cetyl stearate, methyl stearate, isopropyl sebacate, methyl sebacate, sucrose monolaurate, sucrose monostearate, and the like.

Sterols, such as cholesterol, and the like.

Buffers

In general, and as above indicated, buffers for the present compositions include any physiologically acceptable organic acid (and its corresponding salt), either liquid or solid (depending upon application), having a pKa around 3 to 5 including, but not limited to, acetic, fumaric, lactic, citric, propionic, lactic, malic, succinic, and tartaric acids.

Gases

Compositions of this invention can contain air or some other medically/pharmaceutically/cosmetically acceptable gas which is emulsified in a liquid phase of such composition to provide a foam.

Illustrative Buffered Compositions of Metronidazole

A composition of the invention advantageously comprises, in general, at least about 0.1 weight percent metronidazole, based on the total weight of the composition. Preferably metronidazole is present in an amount in the range of about 0.1% to about 2%, more preferably in an amount in the range of about 0.25% to about 1%, and most preferably about 0.75% by weight, based on the total weight of the composition. Larger and smaller contents of metronidazole can be used without departing from the spirit and scope of this invention, however.

Substantially oil-free, aqueous compositions containing metronidazole, in which this drug is solubilized in a single-phase aqueous gel, are a preferred class of embodiments used in the practice of this invention. The overall advantages of such aqueous gel compositions in treating BV have been discussed above, and are presented and illustrated in greater detail hereinbelow.

The actual concentration of metronidazole in any given such composition may vary, depending on variables such as the nature and degree of the BV being treated, the duration of the therapeutic treatment period contemplated, the size of the particular unit dose to be administered, and the like.

In the preferred compositions, metronidazole is in an aqueous solution of a high molecular weight polycarboxylated vinyl polymer. The polymer imparts a desirable viscous, gelled consistency to the composition when mixed with metronidazole and water. The preferred gel compositions contain at least about 95% by weight water, based on the total weight of the composition, and have the requisite degree of metronidazole concentration, and hence thermodynamic activity, for effective topical delivery and bioavailability of metronidazole in the vagina. The preferred gel compositions also have the requisite therapeutic activities as previously described.

The gel-forming polymer useful in compounding such preferred compositions may be any suitable polymer which is hydrophilic and water-dispersible, has free carboxylic groups and relatively high base binding capacity, and forms an aqueous buffered gel of substantially uniform consistency when neutralized with a base. Preferred polymers for use in the compositions of the invention are water-dispersible, polycarboxylated vinyl polymers. Polyacrylic acid polymers are particularly preferred for the present purposes. The molecular weight of the polymer is desirably in the range of about 1,250,000 and about 4,000,000 daltons. Suitable polyacrylic acid polymers include, but are not limited to, polyacrylic acid polymers slightly cross-linked with a polyalkenyl polyether, such as those commercially available from B. F. Goodrich, Cincinnati, Ohio, under the trademarks Carbopol 934, 940, 950 and 941. Carbopol 934P™ is a particularly preferred polymer for use in practicing this invention.

The polymer is present in an amount sufficient to cause gelling of a preferred composition, and to impart the desired viscous consistency to the resulting topical formulation. In addition and importantly, the polymer is used in concentrations that afford the buffering capacity and pH range that are necessary for this method. The metronidazole compositions advantageously comprise about 0.2% to about 7% by weight of the polymer, preferably about 0.5% to about 2.5%, and most preferably about 2% by weight of the polymer based on the total weight of the composition.

Aqueous solutions of these polymers form gels when neutralized with a base. Water-soluble bases which have been used to promote gelling of such polymers as the Carbopols™ include, for example, inorganic bases, such as an aqueous solution of ammonia, NaOH, and organic amine, e.g., alkylamines, such as methylamine and ethylamine, dialkylamines, trialkylamines, alkanolamines, dialkanolamines, and the like. Preferably a strong base is employed. The pharmaceutically effective component of the compositions of the present invention, metronidazole, is itself sufficiently basic to partially neutralize the acidic polymer in aqueous solution to the desired degree and to promote gelling.

optionally, a preferred gel composition may further include a solubilizer, i.e., an agent that promotes penetration of the active drug into the microorganisms. Such solubilizers include, but are not limited to, dimethyl sulfoxide (DMSO) and propylene glycol, with the latter being preferred. The composition advantageously includes about 1% to about 50%, preferably about 2% to about 5%, and more preferably about 3% by weight, of such solubilizer, based on the total weight of the composition.

Preservatives optionally may be incorporated into such gel compositions in an amount effective for inhibiting growth of microbes, such as yeast, molds, and bacteria during gel composition storage. Any conventional preservative may be used, with parabens being preferred. A mixture of methyl paraben and propyl paraben has been found to be particularly effective as a preservative. Most preferably, such a composition comprises about 0.08% by weight of methyl paraben and about 0.02% by weight of propyl paraben based on the total weight of the gel composition.

Ethylenediaminetetraacetic acid (EDTA) or one of its salts is commonly added to dermatological preparations, and may optionally be incorporated into the gel composition. EDTA chelates certain metals that may be present in the formulation, which is useful because some patients have adverse reactions to preparations containing metal impurities. The EDTA will also inhibit undesirable "browning" of the composition which may occur over time in compositions having a low pH value, e.g., a pH value of about 3 to about 4.5. Advantageously, a gel composition optionally further includes from about 0.01% to about 0.1%, preferably about 0.05% by weight, of EDTA based on the total weight of the composition.

The final pH value of a gel composition may vary within the physiologically compatible range. Advantageously, the final pH value is a physiologically compatible, i.e., not harmful to biological tissue, adjusts and controls vaginal environment to normal, healthy range and is acidic. The preferred pH value is about 3.75 to 4.25, more preferably about 4. Any suitable method of adjusting the pH value of aqueous solutions may be used. Advantageously, sodium hydroxide (NaOH) is added to the composition to bring the final pH value to the desired level. The gel compositions are more viscous at pH values that approach neutrality than at the more acidic pH values within the preferred range, i.e., viscosity increases as the polymer in the gel is neutralized to a greater degree, e.g., with NaOH.

The ingredients listed above may be combined in any order and manner that produces a composition comprising metronidazole dissolved in, and evenly dispersed throughout, a one-phase aqueous gel of the desired consistency and pH value. One suitable method of preparing such compositions involves preparation of an aqueous solution of the polymer, which will be called "Part A". Advantageously, this solution comprises the polymer in distilled water. A "Part B" is prepared comprising metronidazole. Mixing of Parts A and B results in gelling of the composition. The optional solubilizer and preservative(s) are preferably included in Part B. If EDTA is to be added to the formulation, it is preferably included in Part A. The pH value may then be adjusted to the desired level, e.g., by addition of NaOH.

The resulting homogeneous buffered gels having a pH in the range indicated possess the advantageous properties described above, including utilizing noninflammatory and non-irritating ingredients. Higher specific activity of metronidazole results due to increased diffusion across membranes, release from the vehicle, and controlled pH. The result is greater therapeutic effectiveness using smaller amount of metronidazole. A formulation has a desirable consistency that prevents undesirable pooling and leaking of metronidazole. High concentrations of tissue-drying ingredients (e.g. alcohols and acetone), which are found, for example, in some preparations to promote drug solubility, are also avoided. Such ingredients at high concentration may excessively dry the patient's vaginal wall causing undesirable discomfort.

As indicated above, when such above described gel composition is introduced as described into an afflicted vagina, a prolonged and surprisingly uniform and regulated (controlled) release rate of metronidazole from the gel composition into the environment of the vagina is achieved. Pooling and running is minimized. The release rate or delivery is sustained for an extended period of time.

The release rate is such that the quantity of the drug which is delivered to vaginal tissues during the release period is at, or slightly above, a minimum therapeutically effective level.

The gel composition also has an unusual and very useful buffering capacity which, in addition to, and in coaction with, the desired bactericidal activity of the metronidazole, is desirable and important in achieving the therapeutic effectiveness that is associated with the practice of this invention. This combination allows for the therapeutic effectiveness of the novel low dose metronidazole formulation by adjusting and controlling the pH of the vaginal environment.

Thus, the gel compositions, as is characteristic of a buffered composition of the invention generally, resist changes in pH upon exposure in the use environment to an acid or a base. In the preparation of a gel composition as above explained herein, a strong base (e.g., sodium hydroxide) is preferably added to the Carbopol™ polymer (weak acid form). This neutralization thickens the formulation to produce the desired gel consistency. It also produces the mixture of components needed to produce a buffered system.

As the exemplary material hereinbelow presented indicates, when a portion of a gel formulation is titrated by a strong base (e.g., sodium hydroxide) successively using each of a concentrated solution of the base and a dilute solution of the base, such that the total volume of base is substantially increased (for example, doubled), it is found not only that there is a significant buffering effect inherent in the gel formulation, but also that there is very little effect on the gel formulation buffer strength as a result of dilution.

These results are significant for purposes of accomplishing topical treatment of, for example, BV by the practice of this invention. For one thing, these results show that the inherent dilution of a unit dose of gel composition which occurs in the vagina does not affect the ability of the gel composition to help prevent and to treat the undesirable alkalinization of the vaginal tissue caused by infections of the BV type. For another thing, these results show that vaginal tissue can be promoted to remain at a pH below about 4.5 which is desirable to inhibit BV organism activity, and to promote certain desirable and normal bacterial colonization and development, such as hydrogen peroxide producing Lactobacilli (Lactobacillus $H_2O_2$+), and the like.

The practice of the present invention is demonstrated in the following examples. These examples are meant to illustrate the invention rather than to limit its scope. Variations in the treating compositions which do not adversely affect the effectiveness of metronidazole will be evident to one skilled in the art, and are within the scope of this invention. For example, additional ingredients such as coloring agents, and the like may be included in the compositions as long as the resulting composition retains desirable properties, as described above. Unless otherwise indicated, each composition is prepared by conventionally admixing the respective indicated components together. Also, unless otherwise indicated, each composition is prepared using a buffer (buffer system) which in use provides a pH value in the range of about 3.75 to about 4.25.

EXAMPLE 1

Gel Preparation

A 30 kilogram batch of a composition of the present invention was prepared as follows. 600 grams of Carbopol 934P™ (2.0% by weight of the final weight of the composition) was dissolved in 16.5 liters of distilled water containing 15 grams of ethylenediaminetetraacetic acid (EDTA) disodium dihydrate. Sufficient amount of 10 weight percent sodium hydroxide (NaOH) solution was added to bring the pH value to about 3.75 to 3.9. This aqueous polymer solution was called "Part A". "Part B" was prepared by mixing 900 grams of propylene glycol (3% by weight of the final weight of the composition), 24 grams of methyl paraben (0.08% by weight of the final weight of the composition) and 6.0 grams of propyl paraben (0.02% by weight of the final weight of the composition). The mixture was added to 225 grams of metronidazole dispersed in 11.4 liters of distilled water maintained at 50° C. Parts A and B were then mixed thoroughly and gelling of the composition resulted. A cold aqueous solution of NaOH was then used to adjust the final pH value to 4.0. Distilled water was then added to give the desired 30 kilogram final weight. The NaOH and water were thoroughly mixed into the viscous gel.

EXAMPLE 2

Oleaginous System Based on Mineral Oil

| Ingredient | Wt % |
| --- | --- |
| Metronidazole | 0.5–1 |
| Colloidal silica | 5.0 |
| Alpha-Tocopherol | 0.1 |
| Tartaric acid/sodium tartrate | 2 |
| Mineral oil 70/80 cps (q.s.) | 100 |

An embodiment of this formulation is prepared by slurrying the metronidazole in the mineral oil and admixing the remaining components therewith.

EXAMPLE 3

Oleaginous Composition

| Ingredient | Wt % |
| --- | --- |
| Metronidazole | 0.5–1 |
| "Aquaphor"* | 50 |
| Methyl Paraben | 0.1 |

-continued

| Ingredient | Wt % |
| --- | --- |
| Propylene Glycol | 3–5 |
| Buffer salts | 10 |
| Water (q.s.) | 100 |

*"Aquaphor" is a trademark of Beiersdorf, Inc., Norwalk, CT for a brand of hydrophilic petrolatum.

EXAMPLE 4

Water-in-Oil (W/O) Emulsion Systems

| W/O Composition I | |
| --- | --- |
| Ingredient | Wt % |
| Oleth-3* | 3.0 |
| Metronidazole | 0.5–1 |
| Buffer salts | 5–10 |
| Laneth 5** | 5.0 |
| Mineral Oil 70/80 | 12.0 |
| Glycerin | 4.0 |
| Methyl Paraben | 0.1 |
| Propyl Paraben | 0.1 |
| Water (q.s.) | 100 |

*"Oleth-3" is the polyethylene glycol ether of oleyl alcohol having an average ethoxylation value of 3.
**"Laneth 5" is the polyethylene glycol ether of lanolin alcohol having an average ethoxylation value of 5.

W/O composition II

| Ingredient | Wt % |
| --- | --- |
| Cholesterol | 1.5 |
| Beeswax | 4.0 |
| Stearyl Alcohol | 1.5 |
| Petrolatum | 43.0 |
| Metronidazole | 0.5–1 |
| Propylene Glycol | 5–10 |
| Acetate Buffer, pH 4.0 | 10 |
| Imidazolidinyl urea | 0.1 |
| Water (q.s.) | 100 |

EXAMPLE 5

Oil-In-Water O/W Emulsions

O/W Composition I

| Ingredient | Wt % |
| --- | --- |
| Metronidazole | 0.5–1 |
| Mineral Oil | 20 |
| Cetyl Alcohol | 2 |
| "Polawax"* | 4 |
| Glycerin | 5 |
| Methyl Paraben | 0.1 |
| Propyl Paraben | 0.05 |
| "Carbopol 934P"** | 0.5–2 |
| NaOH solution 10% q.s. | pH 3.0–4.5 |
| Water (q.s.) | 100 |

*"Polawax" is a trademark of Croda, Inc., New York, N.Y. for a brand of emulsifying wax.
**"Carbopol 937-P" is a trademark of B. F. Goodrich Co. for a brand of acrylic acid polymer crosslinked with a polyfunctional agent.

O/W Composition II

| Ingredient | Wt % |
| --- | --- |
| Metronidazole | 0.5–1 |
| Petrolatum | 5.0 |
| Cetyl Alcohol | 5.0 |
| Sodium Lauryl Sulfate | 0.3 |
| Methyl Paraben | 0.1 |
| Propyl Paraben | 0.1 |
| Acetate Buffer, pH 4.0 | 10 |
| Glycerin | 5 |
| Water (q.s.) | 100 |

O/W Composition III (Transparent Microemulsion)

| Ingredient | Wt % |
| --- | --- |
| Metronidazole | 0.5–1 |
| "Laneth-15"* | 30 |
| Isopropyl Myrestate | 7 |
| Buffer | 5–10 |
| Imidazolidinyl urea | 0.1 |
| Lanolin alcohol | 5 |
| Mineral Oil | 14 |
| Polyethylene Glycol 200 | 5 |
| Water (q.s.) | 100 |

*"Laneth-15" is the polyethylene glycol ether of lanolin alcohol having an average ethoxyation value of 15.

O/W Composition IV (Oil-In-Water Emulsion for Aerosol Foam)

| Ingredient | Wt % |
| --- | --- |
| "Arquad HTL-8"* | 2 |
| Metronidazole | 0.5–1 |
| Buffer | 10 |
| Glycerin | 5 |
| Mineral Oil 70/80 | 3 |
| "Lantrol AWS"** | 2.5 |
| Cetyl Alcohol | 0.25 |
| "Germaben II"*** | 1 |
| Water (q.s.) | 100 |
| Propellants as needed | |

*"Arquad HTL-8" is a trademark of AKZO Chemical America, Chicago, Illinois, for a brand of 2-ethylhexyl dimethyl hydrogenated tallow ammonium chloride.
**"Lantrol AWS" is a trademark of Emery Industries, Inc., Linden, N.J. for a reaction product of lanolin oil with ethylene and propylene oxides to form the trade designated produce "PPG-12--PEG-65."
***"Germaben II" is a trademark of Sutten Laboratories, Inc., Chatham, N.J. for a composition of propylene glycol, diazolidinyl urea, and methyl and propyl parabens.

O/W Composition V

| Ingredient | Wt % |
| --- | --- |
| Metronidazole | 0.5–1 |
| Sorbitol, 70% solution in $H_2O$ | 25 |
| Isopropyl Myristate | 5 |
| Cetyl Alcohol | 8 |
| Glyceryl stearate/PEG-100 stearate | 5 |
| White Petrolatum | 1 |
| Benzyl Alcohol | 1 |
| Aqueous acetate buffer solution, pH 4.0 (q.s.) | 100 |

O/W Composition VI

| Ingredient | Wt % |
| --- | --- |
| Metronidazole | 0.5–1 |
| Glyceryl stearate/PEG-100 stearate | 10 |
| Isopropyl Myristate | 10 |
| Cetyl Alcohol | 1 |
| Methyl Paraben | 0.1 |
| Propyl Paraben | 0.05 |
| Glycerin | 5 |
| "Carbopol 934P" (2%) | 10 |
| Buffer salts | 5–10 |
| NaOH (2%) | 10 |
| Water (q.s.) | 100 |

EXAMPLE 6

Anhydrous Water Soluble Bases

Composition I (Ointment)

| Ingredient | Wt % |
| --- | --- |
| Metronidazole | 0.5–1 |
| Propylene Glycol | 5–10 |
| PEG-400* | 30–40 |
| Potassium Phthalate) (suspended buffer) | 0.1–5 |
| PEG-8000** (q.s.) | 100 |

*"PEG-400" is $H(OCH_2CH_2)_nOH$ where n has an approximate value of 400.
**"PEG-8000" is $H(OCH_2CH_2)OH$ where n has an approximate value of 8000.

Composition II (Gel)

| Ingredient | Wt % |
| --- | --- |
| Metronidazale | 0.5–1 |
| Propylene Glycol | 5–10 |
| Buffer salts | 2–10 |
| Hydroxypropyl cellulose | 0.5–5 |
| Methyl Paraben | 0.1 |
| Glycerin (q.s.) | 100 |

EXAMPLE 7

Aqueous Solutions or Suspensions

Composition I (Buffered Metronidazole Gel Composition; Preferred Embodiment)

| Ingredient | Wt % |
| --- | --- |
| Metronidazole | 0.1–1 |
| "Carbopol 934P" | 1–2 |
| Edetate Disodium | 0.05 |
| Propylene Glycol | 0–15 |
| Methyl Paraben | 0.08 |
| Propyl Paraben | 0.02 |
| NaOH 10% solution (q.s.) | pH 3.75–4.25 |
| Water (q.s.) | 100 |

A composition constituted by the buffer system and the physiologically tolerable medium, but without metronidazole, is also useful as a vaginal acidifier. Such a composition is illustrated below.

Composition II (Buffered Vaginal Acidifier)

(Contains no Metronidazole)

| Ingredient | Wt % |
| --- | --- |
| "Carbopol 934" | 1–5 |
| Edetate Disodium | 0.05 |
| Propylene Glycol | 0–15 |
| Methyl Paraben | 0.08 |
| Propyl Paraben | 0.02 |
| NaCH 10% Solution (q.s.) | pH 3.75–4.25 |
| Water (q.s.) | 100 |

In addition to the above illustrated vaginal acidifier utilizing a gel as the physiologically tolerable medium for the buffer system that is present, the physiologically tolerable medium can be a suppository, a foam, a cream, and the like. For the buffered vaginal acidifier the buffer system is selected so as to provide a buffered pH value in the range of about 3.75 to about 4.25.

Composition III

| Ingredient | Wt % |
| --- | --- |
| Metronidazole | 0.1–1 |
| Methylcellulose 4000 cps | 3 |
| Propylene Glycol | 1–5 |
| Aqueous acetate buffer solution, pH 4.0 (q.s.) | 100 |

Composition IV

| Ingredient | Wt % |
| --- | --- |
| Metronidazole | 0.1–1 |
| "Polyquaternium-10" | 2.5 |
| Aqueous acetate buffer solution, pH 4.0 (q.s.) | 100 |

Composition V (Buffered Solution Administered as a Foam)

Base consists of an oil-in-water emulsion or an aqueous solution or an aqueous suspension of metronidazole and buffer components with a surfactant. The propellant causes the foam to emit preferably as a quick breaking or as a thick, rich foam.

| Ingredient | Wt % |
| --- | --- |
| "Arquad HTL8" | 2.5 |
| Hydroxythyl cellulose | 0.5 |
| Metronidazole | 0.5–1 |
| Propylene Glycol | 5–15 |
| Buffer salts, pH 4.0 | 10 |
| "Kathon CG"* | 0.1 |
| Water (q.s.) | 100 |
| Propellant and foaming agent, as needed | |

*"Kathon CG" is a trademark of Rohm and Haas Co., Inc., Philadelphia, PA for a brand of methylchloroisothiazolinone and methylisolthiazolinone mixture.

EXAMPLE 8

Vaginal Inserts/Suppositories

Composition I (Oleaginous Suppository)

Oil base systems such as cocoa butter or mixtures of hydrogenated fats in which buffer salts are suspended.

| Ingredient | Wt % |
| --- | --- |
| Metronidazole | 0.5–1 |
| Buffer salts | 2–10 |
| Colloidal silica | 2 |
| Cocoa Butter (q.s.) | 100 |

Composition II (Polyethylene Glycol Suppositories)

This system contains mixtures of polyethylene glycols which dissolve in vaginal fluid. The buffer is dissolved or suspended in the P.E.G.

| Ingredient | Wt % |
| --- | --- |
| Metronidazole | 0.5–1 |
| Buffer salts | 2–10 |

-continued

| Ingredient | Wt % |
|---|---|
| "PEG-8000" (30%) "PEG-1540" (70%)* | 100 |

*"PEG-1540" is H(OCH$_2$CH$_2$)$_n$OH where n has a value of about 1540.

Composition III (Glycerin and Glycerinated Gelatin Based Suppositories)

A glycerin-based suppository contains metronidazole and the buffer system dissolved or suspended in approximately 85%–90% glycerin with 5% to 10% sodium stearate. Glycerinated gelatin systems contain the drug and buffer components dissolved or suspended in glycerin and congealed with gelatin.

| Ingredient | Wt % |
|---|---|
| Metronidazole | 0.5–1 |
| Buffer System | 1–10 |
| Glycerogelatin (q.s.) | 100 |

EXAMPLE 9

The Buffering Effect of the Metronidazole Gel Formulation

To determine and demonstrate the effectiveness of the gel composition as a buffer, the following work was carried out:
Procedure:

The gel formulation delineated in Table I below was prepared by the procedure of Example 1 above except for sodium hydroxide addition as described herein, and such was then titrated by the addition of strong base. A titration was carried out on each of two separate batches of the formulation. In one case, the titrant was a concentrated aqueous solution of sodium hydroxide (2.5N). This solution increased the resulting total composition volume only about 8 cc. In the other case, a dilute solution of sodium hydroxide (0.1N) was used as the titrant, which resulted in a doubling of the resulting composition volume from about 100 cc to 200 cc. This procedure allowed an examination of the effects of dilution on the buffer strength of the product.

TABLE I

Metronidazole Gel Formulation

| Component | Percent W/W |
|---|---|
| Metronidazole | 0.75 |
| Propylene Glycol | 3.00 |
| Propyl Paraben | 0.02 |
| Methyl Paraben | 0.08 |
| Disodium EDTA | 0.05 |
| Carbopol 934-P | 1.60 |
| Sodium Hydroxide | a |
| Distilled Water (q.s.) | 100.00 | aSodium hydroxide was omitted from this formulation so that titration could be carried out.

Figure 1:
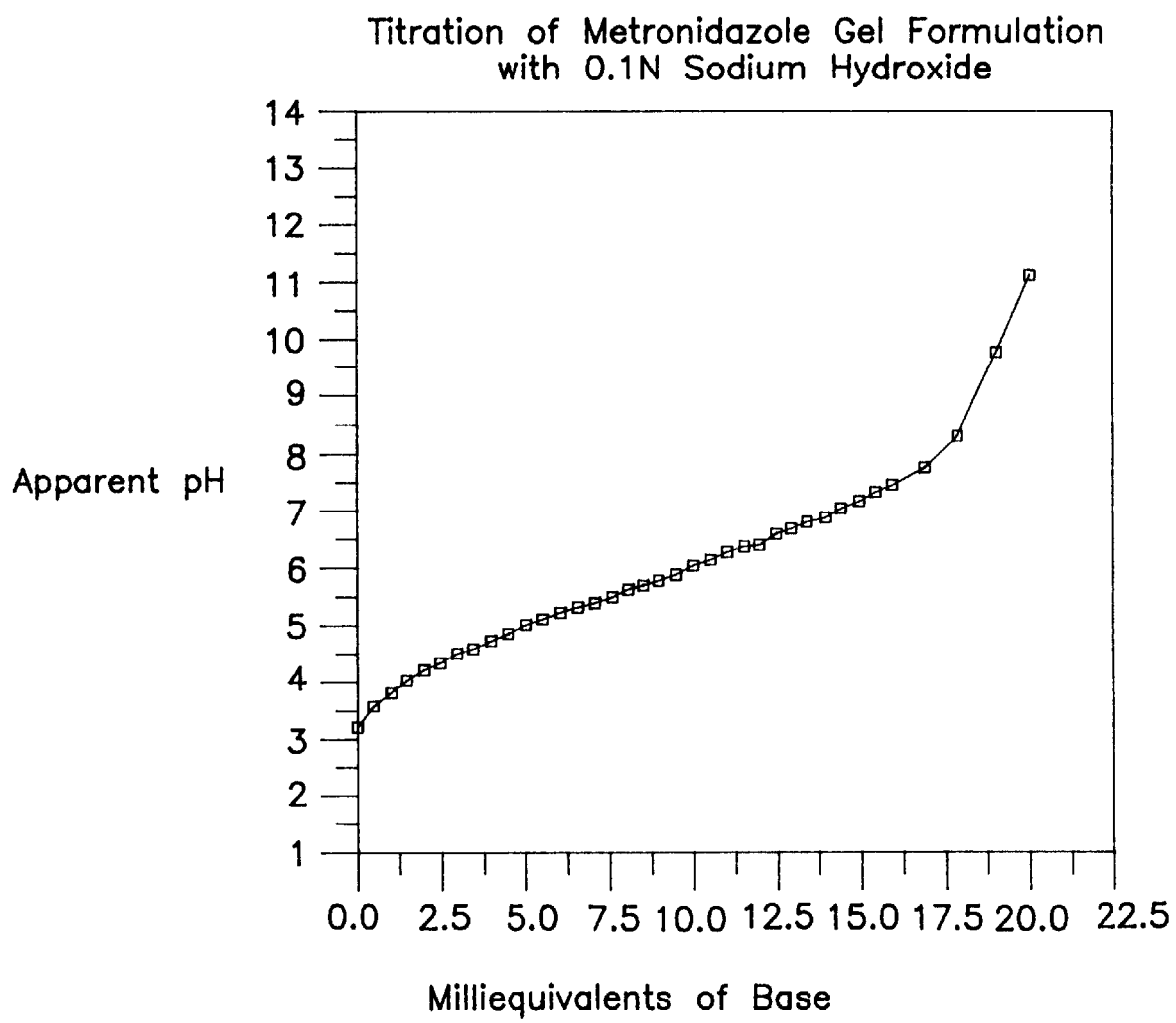
FIG. 1 is a graph illustrating the buffering capacity of a gel composition of the type used in the practice of this invention when titrated with a relatively dilute strong base.

Results:

The titration data that resulted using the 0.1N sodium hydroxide is presented in Table II below and shown in accompanying FIG. 1. The pH range over which there is significant buffering is from about pH 4 to 7.5. The slope in this region is 0.228. The reciprocal of the slope, 4.39, is the buffer capacity. This means that 4.39 mEq of base are needed to change the pH by one unit. The slope in the pH range from 4.05 to 4.92 is 0.285 and the buffer capacity in this region is slightly less at 3.51. The slope in the pH range from 4.92 to 6.89 is 0.213 and the buffer capacity is 4.69.

Figure 2:
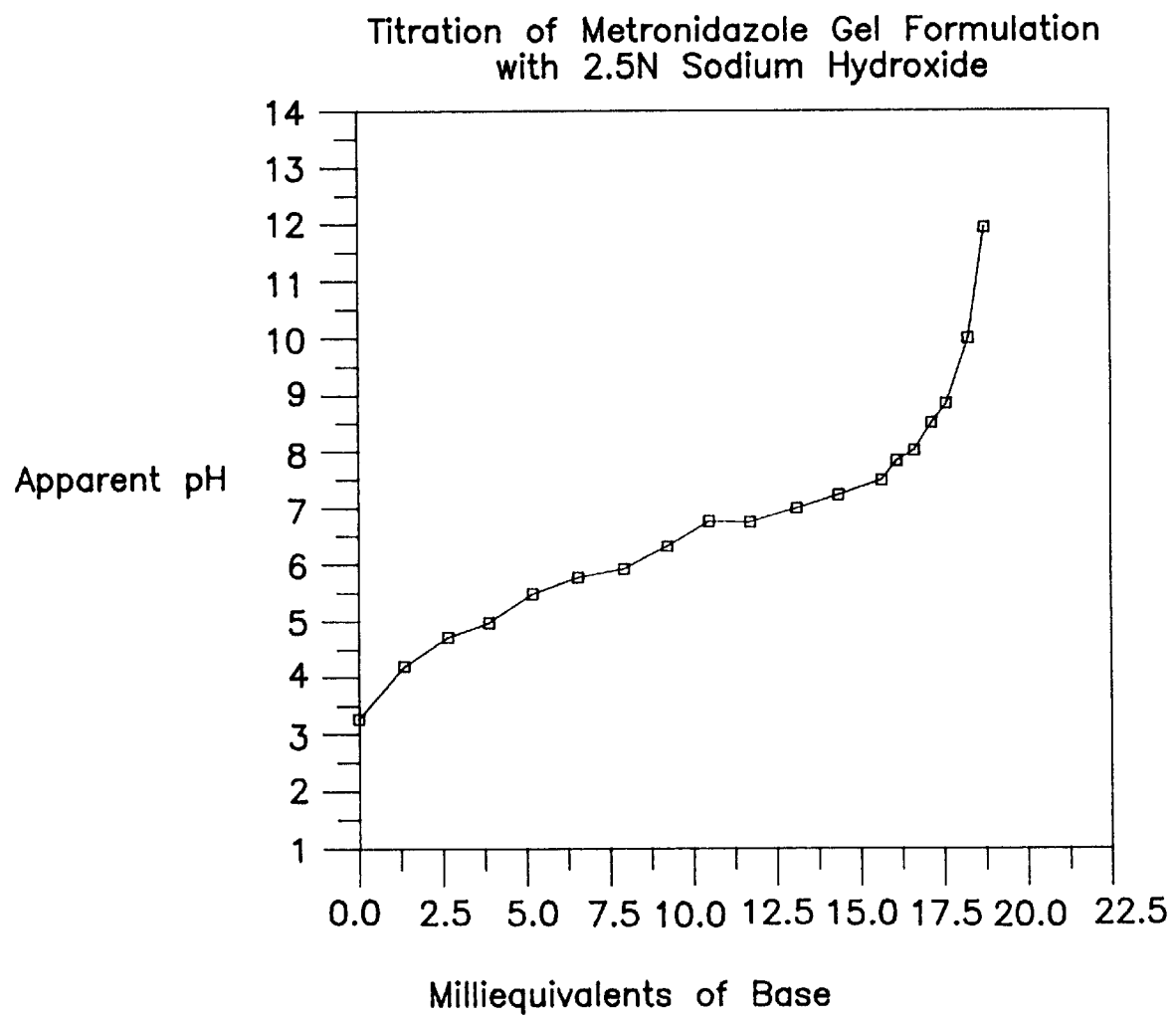
FIG. 2 is a graph illustrating the buffering capacity of the gel composition of FIG. 1 when titrated with a relatively concentrated strong base.

The titration data using the 2.5N sodium hydroxide is presented in Table III and shown in FIG. 2. Again there is a significant buffering effect over a pH range of about 4 to 7.5. The slope of the titration curve in this region is 0.230 and the buffer capacity is 4.36. The slope from pH 4.08 to 4.89 is 0.324 and the buffer capacity is 3.09. The slope in the pH range from pH 4.89 to 6.79 is 0.220 and the buffer capacity is 4.55. This data is very similar to the titration data using the more dilute titrant.

Conclusions:

1. There is a significant buffering effect by the components of the metronidazole gel formulation over a pH range of 4 to 7.5.

2. There is very little effect on the buffer strength of the formulation upon dilution. This is significant since the formulation will become diluted when used, but will not lose its ability to help prevent and treat the alkalinization of the environment caused by infections of the type treated by metronidazole.

TABLE II

Titration Data Using 0.1 N Sodium Hydroxide

| mEq of Base | pH | mEq of Base | pH |
|---|---|---|---|
| 0 | 3.27 | 10.5 | 6.20 |
| 0.5 | 3.57 | 11.0 | 6.33 |
| 1.0 | 3.83 | 11.5 | 6.43 |
| 1.5 | 4.05 | 12.0 | 6.55 |
| 2.0 | 4.22 | 12.5 | 6.67 |
| 2.5 | 4.37 | 13.0 | 6.77 |
| 3.0 | 4.56 | 13.5 | 6.89 |
| 3.5 | 4.65 | 14.0 | 7.01 |
| 4.0 | 4.77 | 14.5 | 7.14 |
| 4.5 | 4.92 | 15.0 | 7.28 |
| 5.0 | 5.07 | 15.5 | 7.43 |
| 5.5 | 5.17 | 16.0 | 7.55 |
| 6.0 | 5.29 | 17.0 | 7.89 |
| 6.5 | 5.39 | 18.0 | 8.36 |
| 7.0 | 5.48 | 19.0 | 9.85 |
| 7.5 | 5.58 | 20.0 | 11.26 |
| 8.0 | 5.68 | | |
| 8.5 | 5.79 | | |
| 9.0 | 5.89 | | |
| 9.5 | 6.00 | | |
| 10.0 | 6.11 | | |

TABLE III

Titration Data Using 2.5 N Sodium Hydroxide

| mEq of Base | pH | mEq of Base | pH |
|---|---|---|---|
| 0 | 3.33 | 12.50 | 6.79 |
| 1.25 | 4.08 | 13.75 | 7.05 |
| 2.50 | 4.64 | 15.00 | 7.30 |
| 3.75 | 4.89 | 15.50 | 7.56 |
| 5.00 | 5.35 | 16.00 | 7.78 |
| 6.25 | 5.54 | 16.50 | 8.20 |
| 7.50 | 5.75 | 17.00 | 8.52 |
| 8.75 | 6.11 | 17.50 | 9.58 |
| 10.00 | 6.53 | 18.00 | 11.42 |
| 11.25 | 6.57 | | |

EXAMPLES 10 AND 11

Clinical Trials: BV

To investigate the effectiveness of the method of this invention for the treatment of BV, the following clinical trials were conducted:

Two groups of human female patients were established. One group was treated for three days; the second group was treated for seven days.

All patients participating in these trials were preliminarily evaluated and were diagnosed to have BV based on positive tests in each patient of at least three of the four standard clinical test criteria employed for diagnosis of BV, as follows:

(1) clue cells comprise at least 20% of vaginal epithelial cells;
(2) homogeneous vaginal discharge;
(3) vaginal pH is greater than or equal to 4.7; and
(4) fishy amine odor appears upon addition of 10% KOH to vaginal discharge.

Each patient was otherwise found to be in good health based on a physical examination and stated medical history.

Only patients thus diagnosed to have solely BV were enrolled in these studies. Thus, patients who evidenced the presence of Candida or trichomoniasis vaginitis, whether concurrently with BV or not, were excluded, as were patients who were (a) involved in any concurrent antibiotic therapy for any condition within 14 days of the start of these studies, or (b) involved in the administration of any investigational drug within 30 days of the start of these studies. Also excluded were patients who had a history of hypersensitivity to metronidazole or to parabens, who were pregnant, who were nursing mothers, who were menstruating at the time of diagnosis, and/or who were unwilling to abstain from sexual intercourse during the treatment phase of the studies.

The vaginal gel used was prepared according to the procedure of Example 1 (above) and such contained 0.75 weight percent metronidazole. Five gram unit dose forms of the gel were administered on a twice daily basis in the morning and evening. Thus, each unit dose contained 37.5 mg of metronidazole.

Each patient was instructed to self-administer two unit doses daily, one in the morning, and one in the evening, for the assigned treatment period.

Each patient was examined at the end of her assigned treatment period. The presence of three of the above-indicated four standard clinical criteria for diagnosis of BV indicated a treatment failure. The lack of three of the above-indicated four standard clinical criteria for diagnosis of BV indicated a treatment success. Each patient was also examined for the presence of local or systemic adverse effects as a result of treatment.

In the three-day treatment, of the 10 patients treated, a 70% success rate was observed.

In the seven-day treatment, of the 11 patients treated, a 100% success rate was observed.

No local or systemic adverse effects were reported in any patients during these trials.

Data from the three-day treatment series is shown in Tables IV and V below (see Table Headings).

Data from the seven-day treatment series is shown in Tables VI and VII below (see Table Headings).

TABLE IV

Vaginal pH Values for Bacterial Vaginosis Patients
Treated for 3 Days with 0.75% Metronidazole Gel Vaginal pH

| Patient Number | (Baseline) Visit #1 | Visit #2 | Visit #3 | Visit #4 |
|---|---|---|---|---|
| 1 | 5.5 | 4.0 | 4.5 | 4.5 |
| 2 | 5.5 | 4.5 | 3.5 | 4.5 |
| 3 | 5.5 | 4.5 | 4.5 | Not taken |
| 4 | 5.5 | 4.5 | 4.0 | 4.0 |
| 5 | 4.5 | 4.0 | 4.0 | 4.0 |
| 6 | 4.5 | 4.5 | 4.5 | Terminated |
| 7 | 4.5 | 4.0 | 4.5 | Terminated |
| 8 | 5.5 | 4.0 | 4.0 | 4.0 |
| 9 | 5.0 | 3.75[1] | 4.25[2] | Not taken |
| 10 | 5.5 | 4.0 | 4.0 | 5.5 |
| n = 10 | n = 10 | n = 10 | n = 10 | n = 6 |
|  | $\bar{x}$ = 5.15 | $\bar{x}$ = 4.18 | $\bar{x}$ = 4.18 | $\bar{x}$ = 4.42 |

[1]Reported as range 3.5 to 4.0.
[2]Reported as range 4.0 to 4.5.

TABLE V

Summary of Results on Bacterial Vaginosis
Patients Treated for 3 Days with 0.75% Metronidaozle Gel

| Patient Number | Visit #2 | | | Visit #3 | | | Visit #4 | | |
|---|---|---|---|---|---|---|---|---|---|
| | Days Since Baseline Visit | Treatment Success Or Failure | | Days Since Last Visit | Days Since Baseline Visit | Treatment Success Or Failure | Days Since Last Visit | Days Since Baseline Visit | Treatment Success Or Failure |
| 1 | 3 | Success | | 17 | 20 | Success* | 14 | 34 | Success[#] |
| 2 | 4 | Success | | 23 | 27 | Success* | 8 | 35 | Success* |
| 3 | 5 | Success | | 11 | 16 | Success* | 18 | 34 | Success* |
| 4 | 7 | Success | | 10 | 17 | Success* | 12 | 29 | Success* |
| 5 | 3 | Success | | 14 | 17 | Success* | 18 | 35 | Success* |
| 6 | 4 | Success | | 14 | 18 | Failure* | — | — | — |
| 7 | 3 | Success | | 14 | 17 | Failure* | — | — | — |
| 8 | 4 | Success | | 14 | 18 | Success | 12 | 30 | Success* |
| 9 | 4 | Success | | 13 | 17 | Success* | 14 | 31 | Success* |

TABLE V-continued

Summary of Results on Bacterial Vaginosis
Patients Treated for 3 Days with 0.75% Metronidaozle Gel

| | Visit #2 | | | Visit #3 | | | Visit #4 | |
|---|---|---|---|---|---|---|---|---|
| Patient Number | Days Since Baseline Visit | Treatment Success Or Failure | Days Since Last Visit | Days Since Baseline Visit | Treatment Success Or Failure | Days Since Last Visit | Days Since Baseline Visit | Treatment Success Or Failure |
| 10 | 3 | Success | 14 | 17 | Success* | 16 | 33 | Failure |
| n = 10 | n = 10<br>x = 4.0<br>(3–7 days) | 10/10 Successes | n = 10<br>x = 14.4<br>(10–23 days) | n = 10<br>x = 18.4 | 8/10 Successes | n = 8<br>x = 14.0<br>(8–18 days) | n = 8<br>x = 32.6 | 7/10 Successes |

*Gram stain showed presence of Gram-positive rods indicative of Lactobacillus.
No Gram stain taken.

TABLE VI

Vaginal pH Values for Bacterial Vaginosis Patients
Treated for 7 Days with 0.75% Metronidazole Gel

| | Vaginal pH | | | |
|---|---|---|---|---|
| Patient Number | Visit #1 | (Baseline) Visit #2 | Visit #3 | Comments |
| 1 | 5.5 | — | — | Dropped |
| 2 | 5.0 | 4.5 | 4.5 | |
| 3 | 4.5 | 4.0 | 4.0 | |
| 4 | 5.5 | 4.0 | 4.0 | |
| 5 | 5.0 | 3.75$^{(1)}$ | 4.0 | |
| 6 | 5.5 | 3.75$^{(1)}$ | 3.5 | |
| 7 | 5.0 | 4.0 | — | Dropped |
| 8 | 5.5 | 4.0 | 4.0 | |
| 9 | 5.0 | 3.5 | — | |
| 10 | 5.5 | 4.0 | 4.5 | |
| 11 | 5.5 | 4.0 | 4.5 | |
| 12 | >5.5 | 4.5 | 5.0 | |
| 13 | 4.5 | 4.0 | 4.5 | |
| n = 13 | n = 13<br>x̄ = 5.2 | n = 12<br>x̄ = 4.0 | n = 10<br>x̄ = 4.3 | |

$^{(1)}$Reported as a range: 3.5 to 4.0.

TABLE VII

Summary of Results on Bacterial Vaginosis
Patients Treated for 7 Days with 0.75% Metronidazole Gel

| Patient Number | Age | Visit #2 Days Since Last Treatment Day | Treatment Success or Failure | Visit #3 Days Since Last Treatment Day | Treatment Success or Failure |
|---|---|---|---|---|---|
| 1 | 25 | 0 | Success | —° | |
| 2 | 20 | 0 | Success* | 8 | Success* |
| 3 | 22 | 0 | Success | 7 | Success* |
| 4 | 18 | 2 | Success* | 24 | Success# |
| 5 | 34 | 3 | Success* | 14 | Success* |
| 6 | 36 | 3 | Success | 17 | Success* |
| 7 | 20 | 10 | Success | —+ | |
| 8 | 24 | 3 | Success* | 18 | Success* |
| 9 | 22 | 12 | Success* | 27 | Success* |
| 10 | 25 | 5 | Success* | 15 | Success* |
| 11 | 19 | 2 | Success* | 14 | Success |
| 12 | 21 | 1 | Success* | 13 | Success* |
| 13 | 23 | 1 | Success* | 15 | Success# |
| n = 13 | x̄ = 23.8 years (18 to 36 years) | x̄ = 3.2 days (0 to 12 days) | 13/13 = Success | x̄ = 15.6 days (7 to 27 days) | 11/11 = Success |

°Dropped: Intrastudy treatment for chlamydia.
+Dropped: Intrastudy treatment for Candida.
*Gram stain showed presence of Gram-positive rods indicative of Lactobacillus.
Gram stain not taken.

EXAMPLE 12

Significance of pH Value for the Vaginal Preparation

The efficacy of 0.75% metronidazole gel for the treatment of bacterial vaginosis was evaluated at pH values of 4 and 6. A double blind study comparing clinical results at both of the aforesaid pH values was carried out. A 5-gram aliquot of metronidazole containing gel (37.5 milligrams of metronidazole) formulated at a pH value of 4, or a pH value of 6, was administered intravaginally twice daily for five days, once in the morning and once in the evening. The gel was based on Carbomer 934P and also contained edetate disodium, methyl paraben, propyl paraben, propylene glycol and sodium hydroxide q.s. to give the desired pH value.

The observed clinical cure rate for clinically evaluable patients 30 days after treatment at pH value of 4 was 88.8 percent (16 patients out of 18 patients) and only 73.3 percent at pH value of 6 (11 patients out of 15 patients). While both cure rates are unexpectedly high in view of the low total amount of metronidazole administered (375 milligrams total dose), the foregoing results underscore clearly the advantage of the relatively lower pH value for the vaginal preparation.

The results of a microbiological evaluation of microbiologically evaluable patients receiving the 0.75% metronidazole gel (n=18 for pH 4 and n=15 for pH 6, respectively) or oral metronidazole are presented in Table VIII, below.

TABLE VIII

Microbiologic Response to Therapy in Women Having Bacterial Vaginosis Treated with Metronidazole Vaginal Gel or Oral Metronidazole

| | Frequency (Concentration CFU/ml) | | |
|---|---|---|---|
| | Metronidazole Vaginal Gel | | Metronidazole Tablets[1] |
| Microorganism | pH 4 n = 18 | pH 6 n = 15 | n = 27 |
| Lactobacillus $H_2O_2$ + | | | |
| Enrollment | 22% ($10^{4.3}$) | 20% ($10^{2.0}$) | 4% ($10^{5.0}$) |
| Follow-up | 61% ($10^{7.2}$) | 33% ($10^{5.4}$) | 52% ($10^{7.2}$) |
| Change | +39% ($10^{2.9}$) | +13% ($10^{3.4}$) | +48% ($10^{2.2}$) |
| Lactobacillus $H_2O_2$ − | | | |
| Enrollment | 55% ($10^{6.5}$) | 53% ($10^{6.5}$) | 37% ($10^{5.9}$) |
| Follow-up | 72% ($10^{6.7}$) | 67% ($10^{6.2}$) | 33% ($10^{6.8}$) |
| Change | +17% ($10^{0.2}$) | +14% ($10^{0.3}$) | +4% ($10^{0.9}$) |
| Bacteroides | | | |
| Enrollment | 94% ($10^{6.7}$) | 87% ($10^{6.5}$) | 78% ($10^{6.7}$) |
| Follow-up | 33% ($10^{3.7}$) | 53% ($10^{3.9}$) | 30% ($10^{4.9}$) |
| Change | −61% (−$10^{3.0}$) | −34% (−$10^{2.6}$) | −48% (−$10^{1.8}$) |
| Peptostreptococcus | | | |
| Enrollment | 94% ($10^{5.9}$) | 93% ($10^{5.6}$) | 63% ($10^{6.6}$) |
| Follow-up | 33% ($10^{3.3}$) | 53% ($10^{3.3}$) | 7% ($10^{4.5}$) |
| Change | −61% (−$10^{2.6}$) | −40% (−$10^{2.3}$) | −56% (−$10^{2.1}$) |
| Gardnerella vaginalis | | | |
| Enrollment | 89% ($10^{8.4}$) | 100% ($10^{8.7}$) | 100% ($10^{8.0}$) |
| Follow-up | 44% ($10^{6.4}$) | 47% ($10^{6.1}$) | 56% ($10^{6.0}$) |
| Change | −55% (−$10^{2.0}$) | −53% (−$10^{2.6}$) | 44% (−$10^{2.0}$) |
| Mycoplasma hominis | | | |
| Enrollment | 39% ($10^{7.0}$) | 47% ($10^{6.7}$) | 48% ($10^{6.5}$) |
| Follow-up | 11% ($10^{4.5}$) | 33% ($10^{4.2}$) | 11% ($10^{3.7}$) |
| Change | −28% (−$10^{2.5}$) | −14% (−$10^{2.5}$) | −37% (−$10^{2.8}$) |
| E. coli | | | |
| Enrollment | 28% ($10^{5.4}$) | 20% ($10^{4.7}$) | 11% ($10^{2.3}$) |
| Follow-up | 28% ($10^{3.4}$) | 13% ($10^{3.0}$) | 33% ($10^{3.7}$) |
| Change | 0% (−$10^{2.0}$) | −7% (−$10^{1.7}$) | +22% (+$10^{1.4}$) |
| Enterococcus | | | |
| Enrollment | 17% ($10^{6.7}$) | 7% ($10^{5.0}$) | 7% ($10^{3.5}$) |
| Follow-up | 28% ($10^{4.4}$) | 40% ($10^{3.7}$) | 48% ($10^{4.0}$) |
| Change | +11% (−$10^{2.3}$) | +33% (−$10^{1.3}$) | +41% (+$10^{0.5}$) |
| Yeast | | | |
| Enrollment | 11% ($10^{5.0}$) | 0% | 11% ($10^{2.3}$) |
| Follow-up | 22% ($10^{4.3}$) | 20% ($10^{3.7}$) | 26% ($10^{3.7}$) |
| Change | +11% (−$10^{0.7}$) | +20% ($10^{3.7}$) | +15% (+$10^{1.4}$) |
| Mobiluncus | | | |
| Enrollment | 6% | 19% | 13% |
| Follow-up | 0% | 0% | 0% |

[1]500 milligrams metronidazole, orally, b. i. d. for 7 days.

The results noted in the foregoing Table are significant in at least several respects.

First, a low dose intravaginal administration of a metronidazole gel at the lower pH value of about 4 provides further benefits as evidenced by the fact that the microbiological profile exhibited by patients treated with an intravaginal low dose of metronidazole formulated at pH 4 is equal or superior to orally administered metronidazole with respect to hydrogen peroxide producing Lactobacillus, Bacteroides, Peptostreptococcus, *Mycoplasma hominis* and yeast, and definitely superior with respect to Enterococcus and *Escherichia coli*.

Secondly, noteworthy is the unexpected albeit beneficial selectivity for Lactobacillus $H_2O_2$+ versus Lactobacillus $H_2O_2$− when metronidazole vaginal gel having a pH value of 4 is used for treatment inasmuch as the restoration of the normal conditions in a healthy vagina is facilitated thereby.

Moreover, the control of the overgrowth of the pathogen Enterococcus was better with the gel composition at pH 4 as compared to the gel composition at pH 6.

The foregoing specification is intended as illustrative and is not to be taken as limiting. Still other variations within the spirit and the scope of the invention are possible and will readily present themselves to those skilled in the art.

Bibliography

Amsel R., Critchlow C. W., Spiegel C. A., Chen K. C. S., Eschenbach D., Smith K., Holmes K. K.; Edited by Finegold S. M., George W. L. and Rolfe R. D., Comparison of metronidazole, ampicillin, and amoxicillin for the treatment of bacterial vaginosis (nonspecific vaginitis): possible explanation for the greater efficacy of metronidazole. Proceedings of the First U.S. Metronidazole Conference. Biomedical Information Corporation (1982).

Amsel R., Critchlow C. W., Spiegel C. A., Chen K. C. S., Eschenbach D., Smith K., Holmes K. K. "Comparison of metronidazole, ampicillin, and amoxicillin for treatment of bacterial vaginosis (nonspecific vaginitis): possible explanation for the greater efficacy of metronidazole." In proceedings of the First U.S. Metronidazole Conference: pp. 225–242. Edited by Finegold S. M, George W. L., and Rolfe R. D. N.Y.: Biomedical Information Corporation (1982).

Balsdon M. J., Pead L., Taylor G. E., et al. "Corynebacterium vaginale and vaginitis: a controlled trial of treatment." Lancet 1:501 (1980).

Bartlett J. G., Polk B. F. Bacterial flora of the vagina: quantitative study. Rev. Infect. Dis. (Suppl 1) 6:S67–S72 (1984).

Bistoletti P., Fredricsson B., Hagstrom B., Nord C. E. "Comparison of oral and vaginal metronidazole therapy for nonspecific bacterial vaginosis." Gynecol. Obstet. Invest. 21:144–149 (1986).

Brenner W. E., Dingfelder J. R., "Metronidazole-containing vaginal sponges for the treatment of bacterial vaginosis," Adv. Contracept. 2:363–369 (1986).

Centers for Disease Control. MMWR Supplement. "1985 STD treatment guidelines." Volume 34 (4S), Oct. 18, 1985.

Charles D., Glover D. D. Antimicrobial treatment of infectious vaginopathies. The Female Patient 10:25–42 (1985).

Davis B., Glover D., Larson B. Analysis of metronidazole penetration into vaginal fluid by reversed-phase high-performance liquid chromatography. Am. J. Obstet. Gynec. 149:802–803 (1984).

Edelman D. A., North B. B., "Treatment of bacterial vaginosis with intravaginal sponges containing metronidazole," J. Reprod. Medicine 34(5):341–344 (1989).

Eschenbach D. A., Critchlow C. W., Watkins H., Smith K., Spiegel C. A., Chen K. C. S., Holmes K. K. "A dose-duration study of metronidazole for the treatment of nonspecific vaginosis." Scand. J. Infect. Dis. (Suppl) 40:73–80 (1983).

Eschenbach D. A., Hillier S., Critchlow C., Stevens C., DeRoven T., Holmes K. K. Diagnosis and clinical manifestations of bacterial vaginosis. Am. J. of Obstet. & Gynecol. 158:819–829 (1988).

Eschenbach D. A., Davick P. R., Williams B. L., Klebanoff S. J., Young-Smith K., Critchlow C. M., Holmes K. K. Prevalence of Hydrogen Peroxide-Producing Lactobacillus Species in Normal Women and Women with Bacterial Vaginosis. J. Clin. Microbiology 27(2):251–256 (1989).

Hagstrom B., Lindstedt J. "Comparison of two different regimens of metronidazole in the treatment of nonspecific vaginitis." Scand. J. Infect. Dis. (Suppl) 40:95–96 (1983).

Hill, L. V. H., Embil J. A. Vaginitis: current microbiological & clinical concepts. Can. Med. Assoc. J. 134:321–331 (1986).

Hillier S. L., North B., Saxena S., "Efficacy of Metronidazole-Containing Sponges for the Treatment of Bacterial Vaginosis." ICAAC Abstract No. 1056, p. 281 (1989).

Larsen B., Galask R. P. Vaginal microbial flora: composition and influence of host physiology. Ann. Intern. Med. 96:926–930 (1982).

Malouf M., Fortier M., Morin G., Dube J-L. "Treatment of Hemophilus vaginalis vaginitis." Obstet. Gynecol. 57(6):711–714 (1981).

Mardh P., Soltesy L. V. In vitro interactions between Lactobacilli and other microorganisms occurring in the vaginal flora. Scand. J. Infect. Dis, (Suppl) 40:47–51 (1983).

Mead P. B., Thomson J. L., Ledger W. J., Eschenbach D. A. "Establishing bacterial vaginosis." Contemp. OB/GYN 27:186–203 (February 1986).

Peeters M., Piot P. Adhesion of Gardnerella vaginalis to vaginal epithelial cells: variables affecting adhesion and inhibition by metronidazole. Genitourin Med. 61:391–395 (1985).

Pheifer T. A., Forsyth P. S., Durfee M. A., Pollock H. M., Holmes K. K. "Nonspecific vaginitis: role of Haemophilus vaginalis and treatment with metronidazole." New Eng. J. Med. 298(26):1429–1434 (1978).

Purdon A., Hanna J. H., Morse D. L., et al. An evaluation of single dose metronidazole treatment for Gardnerella vaginalis vaginitis. Obstet. Gynecol. 64:271 (1984).

Rein M. F. Vulvovaginitis and cervicitis, in Mandell G. L., Douglas R. G., Bennett T. E. (eds). Principles and Practice of Infectious Diseases, Edition 2, New York, John Wiley & Sons Inc., pp. 729–738.

Skavin A., Sylwan J. Vaginal Lactobacilli inhibiting growth of Gardnerella vaginalis, mobiluncus and other bacterial species cultured from vaginal content of women with bacterial vaginosis. Acta. Path. Microbiol. Immunol. Scand., Section B, 94:399–403 (1986).

Staerfelt F., Gundersen T. J., Halsos A. M., Barlinn C., Johansen A. G., Norregaard K. M., Eng, J. A survey of genital infections in patients attending a clinic for sexually transmitted diseases. Scand. J. Infect. Dis. 40:53–57 (1983).

Swedberg J., Steiner J. F., Deiss F., Steiner S., Driggers D. A. "Comparison of single dose versus one week course of metronidazole for symptomatic bacterial vaginosis." JAMA, 258(8):1046–1049 (1985).

Totten P. A., Amsel R., Hales J., Piot P., Holmes K. K. Selective differential human blood filagen media for isolation of Gardnerella vaginalis. J. Clin. Microbiol. 15:141–147 (1982).

I claim:

1. A buffered non-flowing composition suitable for the treatment of bacterial vaginosis which contains metronidazole in a treatment amount of about 375 mg or less wherein the metronidazole is present in a concentration of at least about 0.1 weight percent, based on the weight of the composition, and the metronidazole is present together with a buffer system in a physiologically tolerable medium; said buffer system providing an acidic buffered pH value for the composition in the range of about 3.75 to about 4.25.

2. The composition of claim 1 wherein said physiologically tolerable medium is an oil within which said buffer system and said metronidazole are suspended and/or dissolved.

3. The composition of claim 1 which is an emulsion selected from the group consisting of water-in-oil emulsions and oil-in-water emulsions.

4. The composition of claim 1 which is anhydrous but water soluble.

5. The composition of claim 1 in a gel dosage form.

6. The composition of claim 1 in a suppository dosage form.

7. The composition of claim 1 in a cream dosage form.

8. The composition of claim 1 in a foam dosage form.

9. The composition of claim 1 in the form of a unit dose containing metronidazole in an amount in the range of about 20 to about 100 milligrams.

10. The composition of claim 1 in the form of a unit dose containing metronidazole in an amount in the range of about 20 to about 40 milligrams.

11. The composition of claim 1 in the form of a unit dose containing metronidazole in an amount of about 37.5 milligrams.

12. The composition of claim 1 which has a viscosity at least sufficient to maintain said composition in a substantially non-flowable state at ambient conditions.

13. The composition of claim 1 wherein said composition contains about 0.75 weight percent metronidazole, based on the total weight of the composition.

14. The composition of claim 1 wherein the concentration of metronidazole is in the range of about 0.25 percent to about 1 percent by weight, based on the total weight of the composition.

15. The composition of claim 1 wherein the concentration of metronidazole is in the range of about 0.1 percent to about 2 percent by weight, based on the total weight of the composition.

16. A gel composition suitable for intravaginal treatment of bacterial vaginosis comprising metronidazole in a treatment amount of about 375 mg or less wherein the metronidazole is present in a concentration of at least about 0.1 weight percent based on the weight of the composition and the metronidazole is dispersed in a buffered gelled hydrophilic and water-dispersible polyacrylic acid polymer having free carboxylic acid groups and a molecular weight in the range of about 1,250,000 to about 4,000,000 daltons;

sufficient base to maintain said composition at a pH in the acidic range of about 3.75 to about 4.25; and an aqueous solvent for said metronidazole and said base.

17. The composition of claim 16 wherein the concentration of metronidazole is about 0.75 percent by weight based on the total weight of the composition.

18. The composition of claim 16 wherein the concentration of metronidazole is in the range of about 0.25 percent to about 1 percent by weight based on the total weight of the composition.

19. The composition of claim 17 wherein said polymer is present in a range of about 0.2 percent to about 7 percent by weight based on the total weight of said composition.

20. The composition of claim 16 wherein said polymer is present in a range of about 0.5 percent to about 2.5 percent by weight based on the total weight of said composition.

21. The composition of claim 16 wherein said polymer is present in an amount of about 2 percent by weight based on the total weight of said composition.

22. The composition of claim 16 wherein said gel composition further includes a solubilizer.

23. The composition of claim 22 wherein said solubilizer is propylene glycol and is present in an amount in the range of about 2 percent to about 5 percent by weight, based on the total weight of said composition.

24. The composition of claim 23 wherein said propylene glycol is present in an amount of about 3 percent by weight, based on the total weight of said composition.

25. The composition of claim 16 wherein said gel composition further includes a preservative.

26. The composition of claim 25 wherein said preservative includes at least one paraben.

27. The composition of claim 26 wherein said preservative consists essentially of methyl paraben present in an amount of about 0.08 weight percent and propyl paraben present in an amount of about 0.02 weight percent, based on the total weight of said composition.

28. The composition of claim 16 wherein said gel composition further includes ethylenediamine-tetra acetic acid in an amount in the range of about 0.01 percent to about 0.1 percent by weight, based on the total weight of said composition.

29. The composition of claim 16 in the form of a unit dose which contains about 20 to about 40 milligrams of said metronidazole.

30. The composition of claim 16 in the form of a unit dose which contains about 37.5 milligrams of metronidazole.

31. A method for treating bacterial vaginosis in a human patient which comprises introducing into the vagina of a patient in need of such treatment a non-flowing composition which contains metronidazole in a treatment amount of about 375 mg or less together with a buffer system in a physiologically tolerable medium; said buffer system providing an acidic buffered pH value in the range of about 3.75 to about 4.25, and said composition being introduced into the vagina at least once a day for a time period of at least one day.

32. The method of claim 31 wherein the concentration of metronidazole in said composition is at least about 0.1 weight percent on a total composition weight basis.

33. The method of claim 31 wherein said introducing is carried out one to three times daily over a time period of three to ten days, the total daily dose thus delivered being in the range of about 100 to about 375 milligrams of metronidazole.

34. The method of claim 31 wherein said physiologically tolerable medium comprises an oil within which said metronidazole and said buffer system are suspended and/or dissolved.

35. The method of claim 31 wherein the total dose of metronidazole administered to the patient is in the range of about 185 to about 375 milligrams.

36. A method for the treatment of bacterial vaginosis in a human patient which comprises introducing into the vagina of a patient in need of such treatment a buffered aqueous gel which contains in the range of about 0.1 to about 2 weight percent, based on the total weight of the composition, of metronidazole, and wherein the treatment amount of metronidazole is about 375 mg or less, and a buffer system providing a buffered pH in the range of about 3.75 to about 4.25.

37. The method of claim 36 wherein the composition contains metronidazole in the range of about 0.25 to about 1 weight percent, based on the total weight of the composition.

38. The method of claim 36 wherein the concentration of said metronidazole in said gel composition is about 0.75 percent by weight based on the total weight of said composition.

39. The method of claim 36 wherein said therapeutically effective amount is about 20 to about 40 milligrams of said metronidazole per dose.

40. The method of claim 36 wherein said therapeutically effective amount is about 37.5 milligrams of metronidazole per dose.

41. A method for treating bacterial vaginosis in a human patient which comprises introducing into the vagina of a patient in need of such treatment about 5 grams of a buffered aqueous gel which contains about 0.75 weight percent, based on the total weight of the composition, of metronidazole at an acidic pH value of about 3.75 to about 4.25 once or twice daily for a time period of five days and wherein the treatment amount of metronidazole is about 375 mg or less.

42. An article of manufacture comprising a packaging material and contained therein a pharmaceutical agent containing metronidazole and a buffer system in a physiologically tolerable medium;

said buffer system being capable of providing a buffered pH value in the acidic range of about 3.75 to about 4.25; said pharmaceutical agent being effective for ameliorating the symptoms of bacterial vaginosis; and said packaging material comprising a label which indicates that said pharmaceutical agent can be used for ameliorating the symptoms of bacterial vaginosis in a treatment amount of about 375 mg or less.

43. The article of manufacture in accordance with claim 42 wherein the physiologically tolerable medium is an aqueous gel containing about 0.75 weight percent metronidazole, and said label indicates intravaginal administration once a day for 5 days.

44. A method for preventing bacterial vaginosis which comprises intravaginal administration to a human female patient susceptible to bacterial vaginosis a prophylactic amount of a non-flowing composition which contains metronidazole; said composition having a pH value in the acidic range of about 3.75 to about 4.25 and metronidazole at a concentration of at least about 0.1 weight percent, based on the weight of the composition, wherein the amount of metronidazole administered during each such prophylaxis is about 375 mg or less.

45. The method of claim 44 wherein the metronidazole concentration is in the range of about 0.1 to about 2 weight percent, based on the weight of the composition.

46. The method of claim 44 wherein the metronidazole concentration is in the range of about 0.25 to about 1 weight percent, based on the weight of the composition.

47. The method of claim 44 wherein the metronidazole concentration is about 0.75 weight percent, based on the weight of the composition.

48. The method of claim 44 wherein the amount of metronidazole administered is in the range of about 20 milligrams to about 80 milligrams twice a week on non-consecutive days.

49. The method of claim 44 wherein the amount of metronidazole administered is in the range of about 30 to about 40 milligrams twice a week on non-consecutive days.

* * * * *

UNITED STATES PATENT AND TRADEMARK OFFICE
CERTIFICATE OF CORRECTION

PATENT NO. : 5,840,744
DATED : November 24, 1998
INVENTOR(S) : Robert J. Borgman It is certified that error appears in the above-identified patent and that said Letters Patent is hereby corrected as shown below:

Col. 32, Line 24, "has a viscosity at least" should read --has a viscosity of at least--

Col. 32, Line 45, "acid groups and a molecular" should read --acid groups and molecular--

Col. 32, Line 57, "composition of claim 17" should read --composition of claim 16--

Signed and Sealed this

Fifteenth Day of June, 1999

*Attest:*

Q. TODD DICKINSON

*Attesting Officer*     *Acting Commissioner of Patents and Trademarks*